(12) United States Patent
Nogami et al.

(10) Patent No.: US 11,150,254 B2
(45) Date of Patent: Oct. 19, 2021

(54) METHOD FOR MEASURING REACTIVITY OF FVIII

(71) Applicant: CHUGAI SEIYAKU KABUSHIKI KAISHA, Tokyo (JP)

(72) Inventors: Keiji Nogami, Nara (JP); Midori Shima, Nara (JP); Tetsuhiro Soeda, Shizuoka (JP); Takehisa Kitazawa, Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 15/512,187

(22) PCT Filed: Sep. 24, 2015

(86) PCT No.: PCT/JP2015/076848
§ 371 (c)(1),
(2) Date: Mar. 17, 2017

(87) PCT Pub. No.: WO2016/047652
PCT Pub. Date: Mar. 31, 2016

(65) Prior Publication Data
US 2018/0011114 A1  Jan. 11, 2018

(30) Foreign Application Priority Data
Sep. 26, 2014  (JP) .............................. JP2014-196974

(51) Int. Cl.
*G01N 33/86* (2006.01)
*C07K 16/36* (2006.01)

(52) U.S. Cl.
CPC ............. *G01N 33/86* (2013.01); *C07K 16/36* (2013.01); *C07K 2317/31* (2013.01); *G01N 2333/755* (2013.01); *G01N 2333/9645* (2013.01); *G01N 2333/96444* (2013.01); *G01N 2800/224* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 4,208,479 A | 6/1980 | Maggio et al. |
| 4,444,878 A | 4/1984 | Paulus |
| 4,474,893 A | 10/1984 | Reading |
| 5,496,549 A | 3/1996 | Yamazaki et al. |
| 5,591,828 A | 1/1997 | Bosslet et al. |
| 5,744,446 A | 4/1998 | Lollar et al. |
| 6,005,091 A | 12/1999 | Blackburn et al. |
| 6,010,902 A | 1/2000 | Ledbetter et al. |
| 7,018,632 B2 | 3/2006 | Lindhofer et al. |
| 7,033,590 B1 | 4/2006 | Scheiflinger et al. |
| 7,538,196 B2 | 5/2009 | Jung |
| 7,732,149 B2 | 6/2010 | Kojima et al. |
| 8,030,461 B2 | 10/2011 | Kojima |
| 8,337,841 B2 | 12/2012 | Kojima et al. |
| 8,597,911 B2 | 12/2013 | Miyazaki et al. |
| 9,096,651 B2 | 8/2015 | Igawa et al. |
| 9,334,331 B2 | 5/2016 | Igawa et al. |
| 9,670,269 B2 | 6/2017 | Igawa et al. |
| 10,450,381 B2 | 10/2019 | Igawa et al. |
| 2002/0062010 A1 | 5/2002 | Arathoon et al. |
| 2003/0207346 A1 | 11/2003 | Arathoon et al. |
| 2003/0211460 A1 | 11/2003 | Nelsestuen |
| 2003/0219441 A1 | 11/2003 | Thorpe et al. |
| 2005/0266425 A1 | 12/2005 | Zauderer et al. |
| 2007/0041978 A1 | 2/2007 | Hattori et al. |
| 2008/0075712 A1 | 3/2008 | Hattori et al. |
| 2009/0324589 A1 | 12/2009 | Igawa et al. |
| 2010/0003254 A1 | 1/2010 | Hattori et al. |
| 2010/0015133 A1 | 1/2010 | Igawa et al. |
| 2011/0097754 A1 | 4/2011 | Hilbert et al. |
| 2012/0237517 A1 | 9/2012 | Hattori et al. |
| 2013/0018174 A1 | 1/2013 | Igawa et al. |
| 2013/0330345 A1 | 12/2013 | Igawa et al. |
| 2014/0037632 A1 | 2/2014 | Igawa et al. |
| 2014/0370018 A1 | 12/2014 | Igawa et al. |
| 2015/0240287 A1 | 8/2015 | Soeda et al. |
| 2015/0284465 A1 | 10/2015 | Igawa et al. |
| 2016/0222129 A1 | 8/2016 | Igawa et al. |
| 2016/0229915 A1 | 8/2016 | Igawa et al. |
| 2017/0022293 A1 | 1/2017 | Igawa et al. |
| 2017/0145111 A1 | 5/2017 | Hattori et al. |
| 2017/0275376 A1 | 9/2017 | Igawa et al. |
| 2018/0244800 A1 | 8/2018 | Hattori et al. |
| 2019/0112390 A1 | 4/2019 | Hattori et al. |
| 2019/0315884 A1 | 10/2019 | Igawa et al. |
| 2019/0359728 A1 | 11/2019 | Hattori et al. |
| 2020/0277402 A1 | 9/2020 | Hattori et al. |

FOREIGN PATENT DOCUMENTS

| | | |
|---|---|---|
| CA | 2019559 | 1/2002 |
| CA | 2541671 | 4/2005 |
| CA | 2603264 | 10/2006 |
| CA | 2817964 | 5/2012 |
| CN | 1229646 | 11/2005 |

(Continued)

OTHER PUBLICATIONS

U.S. Appl. No. 15/490,936, Igawa et al., filed Apr. 19, 2017.

(Continued)

*Primary Examiner* — Changhwa J Cheu
(74) *Attorney, Agent, or Firm* — Fish & Richardson P.C.

(57) ABSTRACT

The inventors produced substances that neutralize the activity of a bispecific antibody having an activity of functionally substituting for FVIII, and undertook the construction of methods for measuring the reactivity of FVIII that can ensure accuracy even in the presence of this bispecific antibody. As a result, the inventors discovered that in APTT-based one-stage clotting assay, FVIII activity in the plasma of a hemophilia A patient can be evaluated accurately, and also that in APTT-based Bethesda assay, FVIII inhibitor titer in the plasma of a hemophilia A patient carrying a FVIII inhibitor can be evaluated accurately.

34 Claims, 4 Drawing Sheets

Specification includes a Sequence Listing.

(56) References Cited

FOREIGN PATENT DOCUMENTS

| | | |
|---|---|---|
| CN | 101883793 | 11/2010 |
| CN | 101906160 | 12/2010 |
| CN | 102084254 | 6/2011 |
| CN | 103298937 | 9/2013 |
| CN | 107108746 | 8/2017 |
| EP | 0369566 | 5/1990 |
| EP | 0432134 | 6/1991 |
| EP | 0404097 | 9/1996 |
| EP | 1327681 | 7/2003 |
| EP | 0979281 | 7/2005 |
| EP | 1605058 | 12/2005 |
| EP | 1693448 | 8/2006 |
| EP | 1220923 | 6/2007 |
| EP | 1876236 | 1/2008 |
| EP | 1505148 | 4/2009 |
| EP | 1688488 | 8/2011 |
| EP | 2 238 985 | 8/2012 |
| EP | 2 526 963 | 11/2012 |
| JP | H02-145187 | 6/1990 |
| JP | H05-184383 | 7/1993 |
| JP | H05-199894 | 8/1993 |
| JP | H05-203652 | 8/1993 |
| JP | H05-213775 | 8/1993 |
| JP | H05-304992 | 11/1993 |
| JP | H08-510555 | 11/1996 |
| JP | H10-165184 | 6/1998 |
| JP | H10-511085 | 10/1998 |
| JP | H11-71288 | 3/1999 |
| JP | H11-506310 | 6/1999 |
| JP | 3032287 | 4/2000 |
| JP | 2001-523971 | 11/2001 |
| JP | 2002-518041 | 6/2002 |
| JP | 2003-055398 | 2/2003 |
| JP | 2003-509049 | 3/2003 |
| JP | 2012-082201 | 4/2012 |
| KR | 2013/0102113 | 9/2013 |
| KR | 2013/0102640 | 9/2013 |
| NO | 20062087 | 7/2006 |
| RU | 2339696 | 11/2008 |
| TW | 2007/14313 | 4/2007 |
| TW | 2012/43049 | 11/2012 |
| TW | I 452135 | 9/2014 |
| TW | I 452136 | 9/2014 |
| WO | WO 91/08770 | 6/1991 |
| WO | WO 93/11161 | 6/1993 |
| WO | WO 94/13804 | 6/1994 |
| WO | WO 95/01571 | 1/1995 |
| WO | WO 96/01653 | 1/1996 |
| WO | WO 96/07754 | 3/1996 |
| WO | WO 96/16673 | 6/1996 |
| WO | WO 96/26964 | 9/1996 |
| WO | WO 98/50431 | 11/1998 |
| WO | WO 99/10494 | 3/1999 |
| WO | WO 99/67359 | 12/1999 |
| WO | WO 01/07918 | 2/2001 |
| WO | WO 01/19992 | 3/2001 |
| WO | WO 01/90192 | 11/2001 |
| WO | WO 02/06838 | 1/2002 |
| WO | WO 02/30463 | 4/2002 |
| WO | WO 02/33073 | 4/2002 |
| WO | WO 03/035835 | 5/2003 |
| WO | WO 03/042231 | 5/2003 |
| WO | WO 03/087163 | 10/2003 |
| WO | WO 03/091424 | 11/2003 |
| WO | WO 2004/009618 | 1/2004 |
| WO | WO 2004/060919 | 7/2004 |
| WO | WO 2004/065611 | 8/2004 |
| WO | WO 2004/097041 | 11/2004 |
| WO | WO 2004/111233 | 12/2004 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2006/106905 | 10/2006 |
| WO | WO 2006/109592 | 10/2006 |
| WO | WO 2007/011746 | 1/2007 |
| WO | WO 2007/114319 | 10/2007 |
| WO | WO 2007/114325 | 10/2007 |
| WO | WO 2009/024653 | 2/2009 |
| WO | WO 2009/084659 | 7/2009 |
| WO | WO 2011/078332 | 6/2011 |
| WO | WO 2011/090088 | 7/2011 |
| WO | WO 2012/067176 | 5/2012 |
| WO | WO 2013/131866 | 9/2013 |
| WO | WO 2014/050926 | 4/2014 |
| WO | WO 2015/194233 | 12/2015 |
| WO | WO 2016/047652 | 3/2016 |
| WO | WO 2016/047656 | 3/2016 |
| WO | WO 2016/166014 | 10/2016 |
| WO | WO 2016/171202 | 10/2016 |
| WO | WO 2017/129585 | 8/2017 |
| WO | WO 2017/188356 | 11/2017 |
| WO | WO 2018/181870 | 10/2018 |

OTHER PUBLICATIONS

U.S. Appl. No. 15/512,094, Igawa et al., filed Mar. 23, 2016.
U.S. Appl. No. 11/910,128, Igawa et al., filed Oct. 7, 2008.
U.S. Appl. No. 15/402,580, Hattori et al., filed Jan. 10, 2017.
U.S. Appl. No. 12/295,039, Igawa et al., filed Jan. 20, 2009.
U.S. Appl. No. 14/741,786, Igawa et al., filed Jun. 17, 2015.
U.S. Appl. No. 13/518,861, Igawa et al., filed Oct. 4, 2012.
U.S. Appl. No. 15/132,996, Igawa et al., filed Apr. 19, 2016.
U.S. Appl. No. 15/288,965, Igawa et al., filed Oct. 7, 2016.
U.S. Appl. No. 15/024,063, Igawa et al., filed Mar. 23, 2016.
U.S. Appl. No. 15/319,016, Yoneyama, filed Dec. 15, 2016.
U.S. Pat. No. 9,670,269, Igawa et al., issued Jun. 6, 2017.
U.S. Pat. No. 8,597,911, Miyazaki et al., issued Dec. 3, 2013.
U.S. Pat. No. 9,096,651, Igawa et al., issued Aug. 4, 2015.
U.S. Appl. No. 14/921,590, Hattori et al., filed Oct. 23, 2015.
U.S. Appl. No. 15/172,727, Hattori et al., filed Jun. 3, 2016.
U.S. Appl. No. 15/512,094, Igawa et al., filed Mar. 17, 2017.
Hardisty et al., "A One-stage Factor VIII (Antihaemophilic Globulin) Assay and its Use on Venous and Capillary Plasma," Thromb. Diath. Haemorrh., May 15, 1962;7:215-28.
Kasper et al., "A More Uniform Measurement of Factor VIII Inhibitors," Thromb. Diath. Haemorrh., Dec. 15, 1975;34(3):869-72.
Kitazawa et al., "A bispecific antibody to factors IXa and X restores factor VIII hemostatic activity in a hemophilia A model," Nat Med. Oct. 2012; 18(10):1570-4. doi: 10. 1038/nm. 2942. Epub Sep. 30, 2012.
Manco-Johnson et al., "Prophylaxis versus Episodic Treatment to Prevent Joint Disease in Boys with Severe Hemophilia," N. Engl. J. Med., Aug. 9, 2007;357(6):535-44.
Muto et al., "Anti-factor IXa/X bi specific antibody (ACE910): hemostatic potency against ongoing bleeds in a hemophilia A model and the possibility of routine supplementation," J. Thromb. Haemost., Feb. 2014; 12(2):206-13.
Muto et al., "Anti-factor IXa/X bispecific antibody ACE910 prevents joint bleeds in a long-term primate model of acquired hemophilia A," Blood, Nov. 13, 2014;124(20):3165-71. doi: 10. 1182/blood-2014-07-585737. Epub Oct. 1, 2014.
Oldenburg, "Prophylaxis in bleeding disorders," Thromb. Res., Jan. 2011; 127 Suppl 1:S14-7. do i:10. 1016/j. thromres.2010. 10.005. Epub Nov. 26, 2010.
Sampei et al., "Identification and Multidimensional Optimization of an Asymmetric Bispecific IgG Antibody Mimicking the Function of Factor VIII Cofactor Activity," PLoS One. 2013;8(2):e57479. doi: J10. 1371/journal.pone.0057479. Epub Feb. 28, 2013.
Verbruggen et al., "The Nijmegen Modification of the Bethesda Assay for Factor VIII: C Inhibitors: Improved Specificity and Reliability," Thromb. Haemost., Feb. 1995;73(2):247-51.
Wagenvoord et al., "Development of a Simple Chromogenic Factor VIII Assay for Clinical Use," Haemostasis., 1989;19(4):196-204.
International Search Report in International Application No. PCT/JP2015/076848, dated Dec. 15, 2015, 2 pages.

(56) References Cited

OTHER PUBLICATIONS

International Search Report in International Application No. PCT/JP2015/076854, dated Nov. 24, 2015, 2 pages.
International Preliminary Report on Patentability in International Application No. PCT/JP2015/076854, dated Mar. 28, 2017, 8 pages.
International Preliminary Report on Patentability in International Application No. PCT/JP2015/076848, dated Mar. 28, 2017, 8 pages.
U.S. Appl. No. 15/701,630, Hattori et al., filed Sep. 12, 2017.
U.S. Appl. No. 15/963,345, Hattori et al., filed Apr. 26, 2018.
Muto et al., "Anti-factor IXa/X bispecific antibody (ACE910): hemostatic potency against ongoing bleeds in a hemophilia A model and the possibility of routine supplementation," Supporting Information to J. Thromb. Haemost., Feb. 2014, 12(2):206-13, https://onlinelibrary.wiley.com/action/downloadSupplement?doi=10.1111%2Fjth.12474&attachmentId=2210006855.
U.S. Appl. No. 16/226,798, Hattori et al., filed Dec. 20, 2018.
Muto et al., "Anti-factor lxa/X bispecific antibody (ACE910): hemostatic potency against ongoing bleeds in an hemophilia A model and the possibility of routine supplementation," Journal of Thrombosis and Haemostasis, vol. 12, issue 2, published online Dec. 3, 2013, online version downloaded Feb. 21, 2019, 24 pages.
Muto et al., supporting information for "Anti-factor lxa/X bispecific antibody (ACE910): hemostatic potency against ongoing bleeds in an hemophilia A model and the possibility of routine supplementation," Journal of Thrombosis and Haemostasis, vol. 12, issue 2, published online Dec. 3, 2013, 11 pages.
"National Haemophilia Foundation (NHF) Medical and Scientific Advisory Council (MASAC) Recommendations Concerning Prophylaxis," Medical Bulletin, No. 193, 1 page (1994).
Amersdorfer et al., GenPept Accession No. AAC26541;2001.8.1.
Asselta et al., "Factor V Deficiency," Semin Thromb Hemost. Jun. 2009,35(4):382-9.
Association of Hemophilia Clinic Directors of Canada, "Hemophilia and von Willebrand's Disease: 2. Management," CMAJ. Jul. 15, 1995;153(2):147-57.
Bajaj et al., "A Monoclonal Antibody to Factor IX That Inhibits the Factor VIII:Ca Potentiation of Factor X Activation," J Biol Chem. Sep. 25, 1985,260(21).11574-80.
Bebbington et al., "High-Level. Expression of a Recombinant Antibody From Myeloma Cells Using a Glutamine Synthetase Gene as an Amplifiable Selectable Marker," Biotechnology (NY). Feb. 1992;10(2):169-75.
Bessos et al., "The Characterization of a Panel of Monoclonal Antibodies to Human Coagulation Factor IX," Thromb Res. Dec. 15, 1985;40(6):863-7.
Blazar et al., "Infusion of Anti-87.1 (COBO) and Anti-87.2 (CD86) Monoclonal Antibodies Inhibits Murine Graft-Versus-Host Disease Lethality in Part via Direct Effects on CD4 + and CD8+ T Cells," J Immunol. Oct. 15, 1996;157(8):3250-9.
Bolton-Maggs et al., "Haemophilias A and B," Lancet. May 24, 2003;361 (9371):1801-9.
Borrebaeck et al., "Antibody evolution beyond Nature," Nat Biotechnol. Dec. 2002;20(12):1189-90.
Bos et al., "Enhanced Transfection of a Bacterial Plasmid into Hybridoma Cells by Electroporation: Application for the Selection of Hybrid Hybridoma (Quadroma) Cell Lines," Hybridoma. Feb. 1992;11(1):41-51.
Bowen, "Haemophilia A and haemophilia B: molecular insights," Mol Pathol. Feb. 2002;55(1):1-18.
Brandstetter et al., "X-ray structure of clotting factor IXa: Active site and module structure related to Xase activity and hemophilia B," Proc Natl Acad Sci USA. Oct. 10, 1995;92(21):9796-800.
Brennan et al., "Preparation of Bispecific Antibodies by Chemical Recombination of Monoclonal Immunoglobulin G1 Fragments," Science. Jul. 5, 1985;229(4708):81-3.
Brinkman et al., "Phospholipid-Binding Domain of Factor VIII is Involved in Endothelial Cell-Mediated Activation of Factor X by Factor IXa," Arterioscler Thromb Vasc Biol. Mar. 1, 2002;22(3):511-6.

Carter, "Bispecific human IgG by design," Immunol Methods. Feb. 1, 2001;248(1-2):7-15.
Dahlback, "Blood coagulation," Lancet. May 6, 2000;355(9215):1627-32.
Davie et al., "The Coagulation Cascade: Initiation, Maintenance, and Regulation," Biochemistry. Oct. 29, 1991;30(43):10363-70.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J Immunol. Sep. 15, 2002;169(6):3076-84.
Deng et al., "An Agonist Murine Monoclonal Antibody to the Human c-Mpl Receptor Stimulates Megakaryocytopoiesis," Blood. Sep. 15, 1998;92(6):1981-8.
Ewert et al., "Stability improvement of antibodies for extracellular and intracellular applications: CDR grafting to stable frameworks and structure-based framework engineering," Methods. Oct. 2004;34(2):184-99.
Fay et al., "Nonenzymatic cofactors: factor VIII," Comprehensive Biochemistry, vol. 13, 1986, pp. 35-37.
Fay et al., "The size of human factor VIII heterodimers and the effects produced by thrombin," Biochim Biophys Acta. Jun. 23, 1986;871(3):268-78.
Fay, "Activation of factor VIII and mechanisms of cofactor action," Blood Rev. Mar. 2004;18(1):1-15.
Figini et al., "In Vitro Assembly of Repertoires of Antibody Chains on the Surface of Phage by Renaturation," J Mol Biol. May 27, 1994;239(1):68-78.
Francois et al., "Construction of a Bispecific Antibody Reacting with the α- and β-Chains of the Human IL-2 Receptor," J Immunol. May 15, 1993;150(10):4610-9.
Gelderman et al., "The Inhibitory Effect of CD46, CD55, and CD59 on Complement Activation After Immunotherapeutic Treatment of Cervical Carcinoma Cells with Monoclonal Antibodies or Bispecific Monoclonal Antibodies," Lab Invest. Apr. 2002;82(4):483-93.
Gonzales et al., "Minimizing the Immunogenicity of Antibodies for Clinical Application," Tumour Biol. Jan.-Feb. 2005;26(1):31-43.
Grosse-Hovest et al., "A recombinant bispecific single-chain antibody induces targeted, supra-agonistic CD28-stimulation and tumor cell killing," Eur J Immunol. May 2003;33(5):1334-40.
Hammerling et al., "Use of Hybrid Antibody with Anti-γG and Anti-Ferritin Specificities in Locating Cell Surface Antigens by Electron Microscopy," J Exp Med. Dec. 1, 1968;128(6):1461-73.
Helfrich et al., "A rapid and versatile method for harnessing scFv antibody fragments with various biological effector functions," J Immunol Methods. Apr. 3, 2000;237(1-2):131-45.
Hoad et al., "Characterisation of monoclonal antibodies to human factor X/Xa," J Immunol Methods. Feb. 15, 1991;136(2):269-78.
Holliger et al., ""Diabodies": Small bivalent and bispecific antibody fragments," Proc Natl Acad Sci USA. Jul. 15, 1993;90(14):6444-8.
Hoyer, "The Factor VIII Complex: Structure and Function," Blood. Jul. 1981;58(1):1-13.
Hsia et al., "Treatment of acquired factor X inhibitor by plasma exchange with concomitant intravenous immunoglobulin and corticosteroids," Am J Hematol. Apr. 2008;83(4):318-20.
Hu et al., "Development and Characterization of a Novel Fusion Protein Composed of a Human IgG1 Heavy Chain Constant Region and a Single-Chain Fragment Variable Antibody against Venezuelan Equine Encephalitis Virus," J Biochem. Jan. 2003; 133(1):59-66.
Huse et al., "Generation of a Large Combinatorial Library of the Immunoglobulin Repertoire in Phage Lambda," Science. Dec. 8, 1989;246(4935):1275-81.
Iwahashi et al., "CDR substitutions of a humanized monoclonal antibody (CC49): contributions of individual CDRs to antigen binding and immunogenicity," Mol Immunol. Oct.-Nov. 1999;36(15-16):1079-91.
Janeway et al., "Structure of the Antibody Molecule and Immunoglobulin Genes," Immunobiology, 3rd Edition, Garland Press. 1997:p. 3:1-3:11.
Jirholt et al., "Exploiting sequence space: shuffling in vivo formed complementarity determining regions into a master framework," Gene. Jul. 30, 1998;215(2):471-6.

(56) References Cited

OTHER PUBLICATIONS

Kang et al., "Linkage of recognition and replication functions by assembling combinatorial antibody Fab libraries along phage surfaces," Proc Natl Acad Sci USA. May 15, 1991;88(10):4363-6.
Karpovsky et al., "Production of Target-Specific Effector Cells Using Hetero-Cross Linked Aggregates Containing Anti-Target Cell and Anti-Fcγ Receptor Antibodies," J Exp Med. Dec. 1, 1984;160(6):1686-701.
Kerschbaumer et al., "An Antibody Specific for Coagulation Factor IX Enhances the Activity of the Intrinsic Factor X-activating Complex," J Biol Chem. Sep. 24, 2004;279(39):40445-50. Epub Jul. 20, 2004.
Kim et al., "Mammalian type I interferon receptors consists of two subunits: IFNaR1 and IFNaR2," Gene. Sep. 1, 1997;196(1-2):279-86.
Kroesen et al., "Phase I study of intravenously applied bispecific antibody in renal cell cancer patients receiving subcutaneous interleukin 2," Br J Cancer. Oct. 1994;70(4):652-61.
Kurokawa et al., "Enhanced Fibrinolysis by a Bispecific Monoclonal Antibody Reactive to Fibrin and Tissue Plasminogen Activator," Bio/Technology. Nov. 1989;7:1163-7.
Lacroix-Desmazes et al., "Dynamics of factor VIII interactions determine its immunologic fate in hemophilia A," Blood. Jul. 15, 2008;112(2):240-9. doi: 10.1182/blood-2008-02-124941. EpubMay 9, 2008.
Lapan et al., "Interaction of the A1 Subunit of Factor VIIIa and the Serine Protease Domain of Factor X Identified by Zero-length Cross-linking," Thromb Haemost. Sep. 1998;80(3):418-22.
Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," J Nucl Med. Oct. 1993;34(10):1662-71.
Lenting et al., "The Life Cycle of Coagulation Factor VIII in View of Its Structure and Function," Blood. Dec. 1, 1998;92(11):3983-96.
Lindsay, "Chapter 4: Determination of the Kinetics and Mechanism of tg-FIX Activation by Factor XIa," 49-75 (2004).
Link et al., "Production and Characterization of a Bispecific IgG Capable of Inducing T-Cell-Mediated Lysis of Malignant B Cells," Blood. Jun. 15, 1993;81(12):3343-9.
Lofqvist et al., "Haemophilia prophylaxis in young patients—a long-term follow-up," J Intern Med. May 1997;241(5):395-400.
Lu et al., "Di-diabody: a novel tetravalent bispecific antibody molecule by design," J Immunol Methods. Aug. 2003;279(1-2):219-32.
Lu et al., "Fab-scFv fusion protein: an efficient approach to production of bispecific antibody fragments," J Immunol Methods. Sep. 15, 2002;267(2):213-26.
Massino et al., "Quantitative analysis of the products of IgG chain recombination in hybrid hybridomas based on affinity chromatography and radioimmunoassay," J Immunol Methods. Feb. 14, 1997;201(1):57-66.
Mccafferty et al., "Phage antibodies: filamentous phage displaying antibody variable domains," Nature. Dec. 6, 1990;348(6301):552-4.
Menegatti et al., "Factor X Deficiency," Semin Thromb Hemost. Jun. 2009;35(4):407-15.
Merchant et al., "An efficient route to human bispecific IgG," Nat Biotechnol. Jul. 1998;16(7):677-81.
Mertens et al., "Factor VIII-Factor IX Interactions: Molecular Sites Involved in Enzyme-Cofactor Complex Assembly," Thromb Haemost. Aug. 1999;82(2):209-17.
Milstein et al., "Hybrid hybridomas and their use in immunohistochemistry," Nature. Oct. 6-12, 1983;305(5934):537-40.
Miyazaki et al., "Generation of bispecific IgG, which mimics the cofactor function of blood coagulation factor VIII," Seikagaku, Poster sessions (2P-B-161), Dept. of Genome Antibody Product Res., Chugai Pharmaceutical Co., Ltd., Japan, and Department of Paediatrics, Nara Medical Univ., 2006.
Morrison, "Two heads are better than one," Nat Biotechnol. Nov. 2007;25(11):1233-4.

Nilsson et al., "Induction of split tolerance and clinical cure in high-responding hemophiliacs with factor IX antibodies," Proc Natl Acad Sci USA. Dec. 1986;83(23):9169-73.
Nilsson et al., "Twenty-five years' experience of prophylactic treatment in severe haemophilia A and B," J Intern Med. Jul. 1992;232(1):25-32.
Nitta et al., "Preliminary trial of specific targeting therapy against malignant glioma," Lancet. Feb. 17, 1990;335(8686):368-71.
Okubo et al., "The Production and Characterization of Four Monoclonal Antibodies to Human Factor X," J Nara Med Ass. 1987;38(1):20-28.
Panka et al., "Variable region framework differences result in decreased or increased affinity of variant anti-digoxin antibodies," Proc Natl Acad Sci USA. May 1988;85(9):3080-4.
Paul, "Immunogenicity and Antigen Structure," Fundamental Immunology, 3rd Edition, Raven Press, NY. 1993; Chapter 8: p. 242.
Piper et al., "Interferon Therapy in Primary Care," Prim Care Update Ob Gyns. Jul. 2001;8(4):163-169.
Portolano et al., "Lack of Promiscuity in Autoantigen-Specific H and L Chain Combinations as Revealed by Human H and L Chain "Roulette"," J Immunol. Feb. 1, 1993;150(3):880-7.
Price et al., "Tissue factor and tissue factor pathway inhibitor," Anaesthesia. May 2004;59(5):483-92.
Ridgway et al., "'Knobs-into-holes' engineering of antibody C83 domains for heavy chain heterodimerization," Protein Eng. Jul. 1996;9(7):617-21.
Rudikoff et al., "Single amino acid substitution altering antigen-binding specificity," Proc Natl Acad Sci USA. Mar. 1982;79(6):1979-83.
Ruef et al., "A Bispecific Antifibrin-antiplatelet Urokinase Conjugate (BAAUC) Induces Enhanced Clot Lysis and Inhibits Platelet Aggregation," Thromb Haemost. Jul. 1999;82(1):109-14.
Ruggeri et al., "von Willebrand factor and von Willebrand disease," Blood, Oct. 1987;70(4): 895-904.
Saito et al., "Establishment of Factor VIII Mimetic Antibodies and Their In Vitro Activities in Hemophilia A," 2006 National Hemophilia Foundation Symposia.
Saito et al., "Factor VIII Mimetic Antibody: (1) Establishment and Characterization of Anti-factor IC/anti-factor X Bispecific Antibodies," 2005 International Society of Thrombosis and Haemostasis, vol. 3, Issue Supplements 1, p. OR160.
Sato et al., "Properties of Two VEGF Receptors, Flt-1 and KDR, in Signal Transduction," Ann NY Acad Sci. May 2000;902:201-5; discussion 205-7.
Schmidt et al., "Structure—Function Relationships in Factor IX and Factor IXa," Trends Cardiovasc Med. Jan. 2003;13(1):39-45.
Schmidt et al., Human Physiology, Moscow, 2:431-436 (1996), and English translation: Schmidt et al., "Hemostatis and Coagulation," Human Physiology, R.F. Schmidt, G. Thews.(Eds.), Second, Completely Revised Edition, 418-423 [translated by Marguerite A. Biederman-Thorson], Springer-Verlag (1989).
Schmidt et al., Human Physiology, Moscow, 3:764 (1996), and English translation: Schmidt et al., "Enzymes of the pancreatic juice," Human Physiology, R.F. Schmidt, G. Thews (Eds.), Second, Completely Revised Edition, 716 [translated by Marguerite A. Biederman-Thorson], Springer-Verlag (1989).
Segal et al., "Introduction: bispecific antibodies," J Immunol Methods. Feb. 1, 2001;248(1-2):1-6.
Shalaby et al., "Development of Humanized Bispecific Antibodies Reactive with Cytotoxic Lymphocytes and Tumor Cells Overexpressing the HER2 Protooncogene," J Exp Med. Jan. 1, 1992;175(1):217-25.
Shima et al., "Factor VIII Mimetic Antibody: (2) In Vitro Assessment of Cofactor Activity in Hemophilia A," 2005 International Society of Thrombosis and Haemostasis, vol. 3, Issue Supplement s1, p. P0038.
Shima et al., "Factor VIII Mimetic Antibody: (2) In Vitro Assessment of Cofactor Activity in Hemophilia A," Rinsho Ketsueki. Aug. 30, 2005;46(8):777(#WS-36-5) (with English translation).
Shima, M., "Bispecific antibodies to coagulation factors IXa and X mimic the function of factor VIII," 2006 World Federation of Haemophilia (Haemophilia, 12(Suppl. 2):98 (May 2006)).

(56) References Cited

OTHER PUBLICATIONS

Shirahata, "Direction for Improvement of Coagulation Factor Preparations," Minna ni yakudatsu ketsuyubyo no kiso to rinsho. Iyaku (Medicine and Drug) Journal Co., Ltd. Jan. 15, 2009;280-9 (with English translation).
Soeda et al., "Factor VIII Mimetic Antibody: (1) Establishment of Anti-FIXa/FX Bispecific Antibodies," Rinsho Ketsueki. Aug. 30, 2005;46(8):728(#PL-2-4) (with English translation).
Soeda et al., "FVIII-Mimetic Action of Anti-FIXa/Anti-FX Bispecific Antibodies Produced by the Phage Library Method," Jpn J Thromb Hemost. Oct. 1, 2005;16(5):526(#O-24).
Stickney et al., "Bifunctional Antibody: A Binary Radiopharmaceutical Delivery System for Imaging Colorectal Carcinoma," Cancer Res. Dec. 15, 1991;51(24):6650-5.
Suresh et al., "Advantages of bispecific hybridomas in one-step immunocytochemistry and immunoassays," Proc Natl Acad Sci USA. Oct. 1986;83(20):7989-93.
Suresh et al., "Bispecific Monoclonal Antibodies from Hybrid Hybridomas," Methods Enzymol., Dec. 31, 1986;121:210-28.
Taki, "National Haemophilia Foundation (NHF) Medical and Scientific Advisory Council (MASAC) Recommendations Concerning Prophylaxis," The Journal of Japanese Society on Thrombosis and Hemostasis. Feb. 2, 2002;13(1):109-13.
Tamura et al., "Structural Correlates of an Anticarcinoma Antibody: Identification of Specificity-Determining Residues (SDRs) and Development of a Minimally Immunogenic Antibody Variant by Retention of SDRs Only," J Immunol. Feb. 1, 2000;164(3):1432-41.
Vaughan et al., "Human Antibodies with Sub-nanomolar Affinities Isolated from a Large Non-immunized Phage Display Library," Nat Biotechnol. Mar. 1996;14(3):309-14.
Vehar et al., "Structure of human factor VIII," Nature. Nov. 22-28, 1984;312(5992):337-42.
Weiner et al., "A Human Tumor Xenograft Model of Therapy with a Bispecific Monoclonal Antibody Targeting c-erbB-2 and CD16," Cancer Res. Jan. 1, 993;53(1):94-100.
Weiner et al., "The Role of T Cell Activation in Anti-CD3 X Antitumor Bispecific Antibody Therapy," J Immunol. Mar. 1, 1994;152(5):2385-92.
Wood et al., "Expression of active human factor VIII from recombinant DNA clones," Nature.Nov. 22-28, 1984;312(5992):330-7.
Xiang et al., "Production of Murine V-Human Cr1 Chimeric Anti-Tag72 Antibody Using V Region cDNA Amplified by PCR," Mol Immunol. Aug. 1990;27(8):809-17.
Zhu et al., "An efficient route to the production of an IgG-like bispecific antibody," Protein Eng. May 2000;13(5):361-7.
Chugai Seiyaku Kabushiki Kaisha's letter dated Jun. 12, 2013, regarding oral proceedings scheduled on Jun. 26, 2013, in App. Ser. No.: EP 06730769.4 (Annex A submitted with patentee's letter dated Jun. 12, 2013).
Krudysz-Amblo et al., "Quantitation of anti-factor VIII antibodies in human plasma," Blood, Mar. 2009, 113(11):2587-94. doi: 10.1182/Blood-2008-08-174987. Epub Jan. 14, 2009.
Uchida et al., "A first-in-human phase 1 study of ACE910, a novel factor VIII-mimetic bispecific antibody, in healthy subjects," Blood, Mar. 2016, 127(13):1633-41. doi: 10.1182/blood-2015-06-650226. Epub Dec. 1, 2015.
U.S. Appl. No. 13/518,861, Igawa et al., filed Oct. 4, 2012 (abandoned).
U.S. Pat. No. 8,062,635, Hattori et al., issued Nov. 22, 2011.
U.S. Appl. No. 10/575,905, Hattori et al., filed Apr. 30, 2007 (abandoned).
U.S. Appl. No. 11/910,836, Hattori et al., filed Jan. 12, 2009 (abandoned).
U.S. Appl. No. 13/434,643, Hattori et al., filed Mar. 29, 2012 (abandoned).
U.S. Appl. No. 14/921,590, Hattori et al., filed Oct. 23, 2015 (abandoned).
U.S. Appl. No. 15/172,727, Hattori et al., filed Jun. 3, 2016 (abandoned).
U.S. Appl. No. 15/402,580, Hattori et al., filed Jan. 10, 2017 (abandoned).
U.S. Appl. No. 15/701,630, Hattori et al., filed Sep. 12, 2017 (abandoned).
U.S. Appl. No. 15/963,345, Hattori et al., filed Apr. 26, 2018 (abandoned).
U.S. Appl. No. 16/226,798, Hattori et al., filed Dec. 20, 2018 (abandoned).
U.S. Appl. No. 16/536,385, Hattori et al., filed Aug. 9, 2019.
U.S. Pat. No. 9,334,331, Igawa et al., issued May 10, 2016.
U.S. Appl. No. 14/019,117, Igawa et al., filed Sep. 5, 2013 (abandoned).
U.S. Appl. No. 14/019,712, Igawa et al., filed Sep. 6, 2013 (abandoned).
U.S. Pat. No. 10/450,381, Igawa et al., issued Oct. 22, 2019.
U.S. Appl. No. 15/288,965, Igawa et al., filed Oct. 7, 2016 (abandoned).
U.S. Appl. No. 16/459,791, Igawa et al., filed Jul. 2, 2019.
U.S. Appl. No. 15/512,094, Igawa et al., filed Mar. 23, 2017.
U.S. Appl. No. 16/093,495, Saeki et al., filed Oct. 12, 2018.
U.S. Appl. No. 16/496,089, Shima et al., filed Sep. 20, 2019.
U.S. Appl. No. 16/496,791, Igawa et al., filed Jul. 2, 2019.
U.S. Appl. No. 16/536,385, Igawa et al., filed Aug. 9, 2019.
Davie, "A Brief Historical Review of the Waterfall/Cascade of Blood Coagulation," J Biol Chem, Dec. 19, 2003, 278(51):50819-32. Epub Oct. 21, 2003.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-18.
Gatiyatov et al., "Antiself Antibodies Against Blood Coagulation Factors," Siberian Medical Journal, Jun. 2011, 103(4):34-8 (with English translation).
Goel et al., "Plasticity within the Antigen-Combining Site May Manifest as Molecular Mimicry in the Humoral Immune Response," J Immunol, Dec. 15, 2004, 173(12):7358-67.
Kanyavuz et al., "Breaking the law: unconventional strategies for antibody diversification," Nat Rev Immunol, Jun. 2019, 19(6):355-368. doi: 10.1038/541577-019-0126-7.
Lloyd et al., "Modelling the human immune response: performance of a $10^{11}$ human antibody repertoire against a broad panel of therapeutically relevant antigens,"Protein Eng Des Sel, Mar. 2009, 22(3):159-68. doi: 10.1093/protein/gzn058. Epub Oct. 29, 2008.
USPTO Restriction Requirement in U.S. Appl. No. 15/512,094, dated Feb. 27, 2019, 8 pages.
USPTO Non-Final Office Action in U.S. Appl. No. 15/512,094, dated Oct. 24, 2019, 46 pages.
"Hemostatic Therapy Guideline for Inhibitor-negative Hemophilia Patients," Japanese Journal of Thrombosis and Hemostasis, 2013, 24(6):619-639 (with English translation).
"Hemostatic Therapy Guideline for Inhibitor-positive Hemophilia Patients," Japanese Journal of Thrombosis and Hemostasis, 2013, 24(6):640-658 (with English translation).
ALPROLIX Intravenous, 2019, 16 pages (with English translation).
Astermark et al., "A randomized comparison of bypassing agents in hemophilia complicated by an inhibitor: the FEIBA NovoSeven Comparative (FENOC) Study," Blood, Jan. 15, 2007, 109(2):546-5L Epub Sep. 21, 2006.
Collins et al., "Implications of coagulation factor VIII and IX pharmaco-kinetics in the prophylactic treatment of haemophilia," Haemophilia, Jan. 2011, 17(1):2-10. doi: 10.1111/j.l365-2516.2010.02370.x. Epub Aug. 22, 2010.
Coppola et al., "Acquired Inhibitors of Coagulation Factors: Part I—Acquired Hemophilia A," SeminThromb Hemost, Jul. 2012, 38(5):433-46, doi: 10.1055/s-0032-1315757, Epub Jun. 27, 2012.
Franchini et al., "Acquired haemophilia A: A 2013 update," Thromb Haemost, Dec. 2013, 110(6): 1114-20, doi:10.1160/TH13-05-0363. Epub Sep. 5, 2013.
Guidelines for the Management of Hemophilia, World Federation of Hemophilia, 2005, 52 pages.
Hagiwara et al., "Effect of Emicizumab in improving coagulation ability in the presence of minor amount of Factor IX," Japanese Journal of Thrombosis and Hemostasis, 2017, 28(2):190 0-12 (with English translation).

(56) References Cited

OTHER PUBLICATIONS

Kruse-Jarres, "Inhibitors: our greatest challenge. Can we minimize the incidence?," Haemophilia, Jan. 2013, 19(Suppl 1):2-7. doi: 10.1111/hae.l2049.

Lillicrap, "von Willebrand disease: advances in pathogenetic understanding, diagnosis, and therapy," Blood, Nov. 28, 2013, 122(23):3735-40. doi: 10.1182/blood-2013-06-498303. Epub Sep. 24, 2013.

Minami et al., "Bispecific Antibody ACE910 Improves Coagulation Function in Plasma of Patients with Factor XI-Deficiency," Japanese Journal of Thrombosis and Hemostasis, 2015, 26(2): 188 0-024 (with English translation).

Miyata, "Factor IX Abnormality—Molecular defects of Factor IX," Japanese Journal of Thrombosis and Hemostasis, 1991, 2(1):1-11 (with English translation).

Nishimura et al., "Factor IX Fukuoka—Substitution of ASN92 by his in the second epidermal growth factor-like domain results in defective interaction with factors VIIIa/X," J Biol Chem, Nov. 15, 1993, 268(32):24041-24046.

Nogami, "Bispecific Antibody that Substitutes for Factor VIII in the Treatment of Childhood Hemophilia A," The Japanese Journal of Pediatric Hematology/Oncology, 2016, 53(2):69-74 (with English translation).

Shima et al., "Factor VIII-Mimetic Function of Humanized Bispecific Antibody in Hemophilia A," N Engl J Med, May 26, 2016, 374(21):2044-2053, doi: 10.1056/NEJMoal511769.

Shima, "The Forefront and Prospects of Hemophilia Treatment," J Jpn Pediatr Soc, Mar. 1, 2017, 121(3):543-552 (with English translation).

Tarantino et al., "Safety of human plasma-derived clotting factor products and their role in haemostasis in patients with haemophilia: meeting report," Haemophilia, Sep. 2007, 13(5):663-9.

U.S. Appl. No. 16/825,513, Hattori et al., filed Mar. 20, 2020.

USPTO Final Office Action in U.S. Appl. No. 15/512,094, dated Jul. 14, 2020, 10 pages.

U.S. Appl. No. 17/130,736 filed Dec. 22, 2020, Hattori et al.

Taylor et al., "A new era for hemophilia B treatment," Blood, Apr. 7, 2016, 127(14): 1734-1736.

USPTO Non-Final Office Action in U.S. Appl. No. 15/512,094, dated Mar. 25, 2021, 9 pages.

SEQUENCE LISTING

<160> NUMBER OF SEQ ID NOS: 38

<210> SEQ ID NO 1
<211> LENGTH: 124
<212> TYPE: PRT
<213> ORGANISM: Artificial
<220> FEATURE:
<223> OTHER INFORMATION: AQ8 VH

<400> SEQUENCE: 1

```
Glu Val Asn Leu Val Glu Ser Gly Gly Gly Leu Val Gln Pro Gly Gly
1               5                   10                  15

Ser Met Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Ala Leu Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Ala Arg Asp Ser Tyr Tyr Ser Tyr Asp Gly Tyr Ala Met Asp
            100                 105                 110

Tyr Trp Gly Gln Gly Thr Ser Val Thr Val Ser Ser
        115                 120
```

<210> SEQ ID NO 2
<211> LENGTH: 107
<212> TYPE: PRT
<213> ORGANISM: Artificial
<220> FEATURE:
<223> OTHER INFORMATION: AQ8 VL

<400> SEQUENCE: 2

```
Asp Ile Gln Met Thr Gln Ser Pro Ala Ser Leu Ala Ala Ser Val Gly
1               5                   10                  15

Glu Thr Ile Thr Ile Thr Cys Gln Ala Ser Glu Asn Ile Tyr Phe Ser
            20                  25                  30

Leu Ala Trp Tyr Gln Gln Lys Gln Gly Lys Ser Pro Gln Leu Leu Ile
        35                  40                  45

Tyr Asn Thr Asp Ser Leu Lys Asp Gly Val Pro Ser Arg Phe Ser Gly
    50                  55                  60

Ser Gly Ser Gly Thr Gln Tyr Ser Met Lys Ile Asn Ser Met Gln Pro
65                  70                  75                  80

Glu Asp Thr Ala Thr Tyr Phe Cys Arg Gln Ser Tyr Asp Phe Pro Trp
                85                  90                  95

Thr Phe Gly Gly Gly Thr Lys Leu Glu Ile Lys
            100                 105
```

<210> SEQ ID NO 3
<211> LENGTH: 120
<212> TYPE: PRT
<213> ORGANISM: Artificial
<220> FEATURE:
<223> OTHER INFORMATION: AJ540 VH

<400> SEQUENCE: 3

```
Gln Ile Gln Leu Val Gln Ser Gly Pro Glu Leu Lys Lys Pro Gly Glu
1               5                   10                  15
Ser Val Lys Ile Ser Cys Lys Ala Ser Gly Tyr Thr Phe Thr Asp Tyr
            20                  25                  30
Ala Met His Trp Val Lys Gln Val Pro Gly Lys Gly Leu Lys Trp Met
        35                  40                  45
Gly Trp Ile Asn Thr Tyr Thr Gly Lys Pro Tyr Ala Asp Asp Phe
    50                  55                  60
Lys Gly Arg Phe Val Phe Ser Leu Glu Ala Ser Ala Ser Thr Ala Asn
65                  70                  75                  80
Leu Gln Ile Ser Asn Leu Lys Asn Glu Asp Thr Ala Asn Val Phe Cys
                85                  90                  95
Ala Arg Glu Gly Gly Gly Tyr Tyr Trp Tyr Phe Asp Phe Trp Gly Pro
            100                 105                 110
Gly Thr Met Val Thr Val Ser Ser
        115                 120
```

<210> SEQ ID NO 4
<211> LENGTH: 107
<212> TYPE: PRT
<213> ORGANISM: Artificial
<220> FEATURE:
<223> OTHER INFORMATION: AJ540 VL

<400> SEQUENCE: 4

```
Asp Ile Val Met Thr Gln Ser Pro Thr Ser Met Ser Ile Ser Val Gly
1               5                   10                  15
Asp Arg Val Thr Met Asn Cys Lys Ala Asn Gln Asn Val Asp Phe Asn
            20                  25                  30
Val Asp Trp Tyr Gln Gln Lys Thr Gly Gln Ser Pro Lys Leu Leu Ile
        35                  40                  45
Tyr Lys Ala Ser Asn Arg Tyr Thr Gly Val Pro Asp Arg Phe Thr Gly
    50                  55                  60
Ser Gly Ser Gly Thr Asp Phe Thr Phe Thr Ile Ser Asn Met Gln Ala
65                  70                  75                  80
Glu Asp Leu Ala Val Tyr Tyr Cys Met Gln Ser Asn Ser Phe Pro Leu
                85                  90                  95
Thr Phe Gly Ser Gly Thr Asn Leu Glu Ile Lys
            100                 105
```

<210> SEQ ID NO 5
<211> LENGTH: 372
<212> TYPE: DNA
<213> ORGANISM: Artificial
<220> FEATURE:
<223> OTHER INFORMATION: nucleic acid sequence of AQ8 VH

<400> SEQUENCE: 5

```
gaagtgaacc tggtggaaag cggcggaggc ctggtgcagc ccggaggcag catgtctctg      60
agctgcgccg ccagcggctt caccttcacc gactactaca tgagctgggt ccgccagccc     120
cctggcaagg ctctggaatg gctggctctg atcagaaaca aggccaacgg ctacaccacc     180
gagtacagcg ccagcgtgaa gggccggttc accatcagcc gggacaacag ccagagcatc     240
ctgtacctgc agatgaacgc cctgcgggcc gaggactccg ccacctacta ctgcgccaga     300
```

```
gacagctact acagctacga cggctacgcc atggactact ggggccaggg caccagcgtg    360
accgtgtcta gc                                                        372
```

<210> SEQ ID NO 6
<211> LENGTH: 321
<212> TYPE: DNA
<213> ORGANISM: Artificial
<220> FEATURE:
<223> OTHER INFORMATION: nucleic acid sequence of AQ8 VL

<400> SEQUENCE: 6

```
gacatccaga tgacccagag ccctgcctcc ctggccgcct ctgtgggcga gacaatcacc     60
atcacctgtc aggccagcga gaacatctac ttcagcctgg cctggtatca gcagaagcag    120
ggcaagagcc cccagctgct gatctacaac accgacagcc tgaaggacgg cgtgcccagc    180
agattcagcg gcagcggctc cggcacccag tacagcatga agatcaacag catgcagccc    240
gaggacaccg ctacctactt ttgccggcag agctacgact cccctggac cttcggcgga     300 ggcaccaagc tggaaatcaa g                                              321
```

<210> SEQ ID NO 7
<211> LENGTH: 360
<212> TYPE: DNA
<213> ORGANISM: Artificial
<220> FEATURE:
<223> OTHER INFORMATION: nucleic acid sequence of AJ540 VH

<400> SEQUENCE: 7

```
cagatccagc tggtgcagag cggccctgag ctgaagaaac ccggcgagag cgtgaagatc     60
agctgcaagg ccagcggcta caccttcacc gactacgcca tgcactgggt gaaacaggtg    120
cccggcaagg gcctgaagtg gatgggctgg atcaacacct acaccggcaa gcccacctac    180
gccgacgact caagggcag attcgtgttc agcctggaag ccagcgccag caccgccaac    240
ctgcagatca gcaacctgaa gaacgaggac accgccaacg tgttctgcgc cagagagggc    300
ggaggctact actggtactt cgacttctgg ggccctggca atggtgac agtgtccagc     360
```

<210> SEQ ID NO 8
<211> LENGTH: 321
<212> TYPE: DNA
<213> ORGANISM: Artificial
<220> FEATURE:
<223> OTHER INFORMATION: nucleic acid sequence of AJ540 VL

<400> SEQUENCE: 8

```
gacatcgtga tgacccagag ccccaccagc atgagcatca gcgtgggcga cagagtgacc     60
atgaactgca aggccaacca gaacgtggac ttcaacgtgg actggtatca gcagaaaacc    120
ggccagtccc ccaagctgct gatctacaag gccagcaacc ggtacacagg cgtgcccgac    180
agattcacag gcagcggcag cggcaccgac ttcaccttca ccatcagcaa catgcaggcc    240
gaggacctgg ccgtgtacta ctgcatgcag agcaacagct cccccctgac cttcggctcc    300
ggcaccaacc tggaaatcaa g                                              321
```

<210> SEQ ID NO 9
<211> LENGTH: 448
<212> TYPE: PRT
<213> ORGANISM: Artificial
<220> FEATURE:
<223> OTHER INFORMATION: Amino acid sequence of antibody heavy chain

<400> SEQUENCE: 9

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Lys Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

Lys Ser Arg Trp Gln Glu Gly Asn Val Phe Ser Cys Ser Val Met His
            420                 425                 430

Glu Ala Leu His Asn Arg Tyr Thr Gln Lys Ser Leu Ser Leu Ser Pro
            435                 440                 445

<210> SEQ ID NO 10
<211> LENGTH: 214
<212> TYPE: PRT
<213> ORGANISM: Artificial
<220> FEATURE:
<223> OTHER INFORMATION: Amino acid sequence of antibody heavy chain

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
            35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 11
<211> LENGTH: 444
<212> TYPE: PRT
<213> ORGANISM: Artificial
<220> FEATURE:
<223> OTHER INFORMATION: Amino acid sequence of antibody light chain

<400> SEQUENCE: 11

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
            35                  40                  45

Gly Asp Ile Asn Thr Arg Ser Gly Gly Ser Ile Tyr Asn Glu Glu Phe
    50                  55                  60

```
Gln Asp Arg Val Ile Met Thr Val Asp Lys Ser Thr Asp Thr Ala Tyr
 65                  70                  75                  80

Met Glu Leu Ser Ser Leu Arg Ser Glu Asp Thr Ala Thr Tyr His Cys
                 85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Pro
        435                 440

<210> SEQ ID NO 12
<211> LENGTH: 5
<212> TYPE: PRT
<213> ORGANISM: Artificial
<220> FEATURE:
<223> OTHER INFORMATION: AQ8 heavy chain CDR1
```

<400> SEQUENCE: 12

Asp Tyr Tyr Met Ser
1               5

<210> SEQ ID NO 13
<211> LENGTH: 19
<212> TYPE: PRT
<213> ORGANISM: Artificial
<220> FEATURE:
<223> OTHER INFORMATION: AQ8 heavy chain CDR2

<400> SEQUENCE: 13

Leu Ile Arg Asn Lys Ala Asn Gly Tyr Thr Thr Glu Tyr Ser Ala Ser
1               5                   10                  15

Val Lys Gly

<210> SEQ ID NO 14
<211> LENGTH: 13
<212> TYPE: PRT
<213> ORGANISM: Artificial
<220> FEATURE:
<223> OTHER INFORMATION: AQ8 heavy chain CDR3

<400> SEQUENCE: 14

Asp Ser Tyr Tyr Ser Tyr Asp Gly Tyr Ala Met Asp Tyr
1               5                   10

<210> SEQ ID NO 15
<211> LENGTH: 15
<212> TYPE: DNA
<213> ORGANISM: Artificial
<220> FEATURE:
<223> OTHER INFORMATION: nucleic acid sequence of AQ8 heavy chain CDR1

<400> SEQUENCE: 15
gactactaca tgagc                                                    15

<210> SEQ ID NO 16
<211> LENGTH: 57
<212> TYPE: DNA
<213> ORGANISM: Artificial
<220> FEATURE:
<223> OTHER INFORMATION: nucleic acid sequence of AQ8 heavy chain CDR2

<400> SEQUENCE: 16
ctgatcagaa acaaggccaa cggctacacc accgagtaca gcgccagcgt gaagggc      57

<210> SEQ ID NO 17
<211> LENGTH: 39
<212> TYPE: DNA
<213> ORGANISM: Artificial
<220> FEATURE:
<223> OTHER INFORMATION: nucleic acid sequence of AQ8 heavy chain CDR3

<400> SEQUENCE: 17
gacagctact acagctacga cggctacgcc atggactac                          39

<210> SEQ ID NO 18
<211> LENGTH: 11
<212> TYPE: PRT
<213> ORGANISM: Artificial
<220> FEATURE:
<223> OTHER INFORMATION: AQ8 light chain CDR1

<400> SEQUENCE: 18

Gln Ala Ser Glu Asn Ile Tyr Phe Ser Leu Ala
1               5                   10

<210> SEQ ID NO 19
<211> LENGTH: 7
<212> TYPE: PRT
<213> ORGANISM: Artificial
<220> FEATURE:
<223> OTHER INFORMATION: AQ8 light chain CDR2

<400> SEQUENCE: 19

Asn Thr Asp Ser Leu Lys Asp
1               5

<210> SEQ ID NO 20
<211> LENGTH: 9
<212> TYPE: PRT
<213> ORGANISM: Artificial
<220> FEATURE:
<223> OTHER INFORMATION: AQ8 light chain CDR3

<400> SEQUENCE: 20

Arg Gln Ser Tyr Asp Phe Pro Trp Thr
1               5

<210> SEQ ID NO 21
<211> LENGTH: 33
<212> TYPE: DNA
<213> ORGANISM: Artificial
<220> FEATURE:
<223> OTHER INFORMATION: nucleic acid sequence of AQ8 light chain CDR1

<400> SEQUENCE: 21
caggccagcg agaacatcta cttcagcctg gcc                            33

<210> SEQ ID NO 22
<211> LENGTH: 21
<212> TYPE: DNA
<213> ORGANISM: Artificial
<220> FEATURE:
<223> OTHER INFORMATION: nucleic acid sequence of AQ8 light chain CDR2

<400> SEQUENCE: 22
aacaccgaca gcctgaagga c                                         21

<210> SEQ ID NO 23
<211> LENGTH: 27
<212> TYPE: DNA
<213> ORGANISM: Artificial
<220> FEATURE:
<223> OTHER INFORMATION: nucleic acid sequence of AQ8 light chain CDR3

<400> SEQUENCE: 23
cggcagagct acgacttccc ctggacc                                   27

<210> SEQ ID NO 24
<211> LENGTH: 5
<212> TYPE: PRT
<213> ORGANISM: Artificial
<220> FEATURE:
<223> OTHER INFORMATION: AJ540 heavy chain CDR1

<400> SEQUENCE: 24

Asp Tyr Ala Met His
1               5

```
<210> SEQ ID NO 25
<211> LENGTH: 17
<212> TYPE: PRT
<213> ORGANISM: Artificial
<220> FEATURE:
<223> OTHER INFORMATION: AJ540 heavy chain CDR2

<400> SEQUENCE: 25

Trp Ile Asn Thr Tyr Thr Gly Lys Pro Thr Tyr Ala Asp Asp Phe Lys
1               5                   10                  15

Gly

<210> SEQ ID NO 26
<211> LENGTH: 11
<212> TYPE: PRT
<213> ORGANISM: Artificial
<220> FEATURE:
<223> OTHER INFORMATION: AJ540 heavy chain CDR3

<400> SEQUENCE: 26

Glu Gly Gly Gly Tyr Tyr Trp Tyr Phe Asp Phe
1               5                   10

<210> SEQ ID NO 27
<211> LENGTH: 15
<212> TYPE: DNA
<213> ORGANISM: Artificial
<220> FEATURE:
<223> OTHER INFORMATION: nucleic acid sequence of AJ540 heavy chain CDR1

<400> SEQUENCE: 27
gactacgcca tgcac                                                    15

<210> SEQ ID NO 28
<211> LENGTH: 51
<212> TYPE: DNA
<213> ORGANISM: Artificial
<220> FEATURE:
<223> OTHER INFORMATION: nucleic acid sequence of AJ540 heavy chain CDR2

<400> SEQUENCE: 28
tggatcaaca cctacaccgg caagcccacc tacgccgacg acttcaaggg c             51

<210> SEQ ID NO 29
<211> LENGTH: 33
<212> TYPE: DNA
<213> ORGANISM: Artificial
<220> FEATURE:
<223> OTHER INFORMATION: nucleic acid sequence of AJ540 heavy chain CDR3

<400> SEQUENCE: 29
gagggcggag gctactactg gtacttcgac ttc                                33

<210> SEQ ID NO 30
<211> LENGTH: 11
<212> TYPE: PRT
<213> ORGANISM: Artificial
<220> FEATURE:
<223> OTHER INFORMATION: AJ540 light chain CDR1

<400> SEQUENCE: 30

Lys Ala Asn Gln Asn Val Asp Phe Asn Val Asp
1               5                   10
```

```
<210> SEQ ID NO 31
<211> LENGTH: 7
<212> TYPE: PRT
<213> ORGANISM: Artificial
<220> FEATURE:
<223> OTHER INFORMATION: AJ540 light chain CDR2

<400> SEQUENCE: 31

Lys Ala Ser Asn Arg Tyr Thr
1               5

<210> SEQ ID NO 32
<211> LENGTH: 9
<212> TYPE: PRT
<213> ORGANISM: Artificial
<220> FEATURE:
<223> OTHER INFORMATION: AJ540 light chain CDR3

<400> SEQUENCE: 32

Met Gln Ser Asn Ser Phe Pro Leu Thr
1               5

<210> SEQ ID NO 33
<211> LENGTH: 33
<212> TYPE: DNA
<213> ORGANISM: Artificial
<220> FEATURE:
<223> OTHER INFORMATION: nucleic acid sequence of AJ540 light chain CDR1

<400> SEQUENCE: 33
aaggccaacc agaacgtgga cttcaacgtg gac                                   33

<210> SEQ ID NO 34
<211> LENGTH: 21
<212> TYPE: DNA
<213> ORGANISM: Artificial
<220> FEATURE:
<223> OTHER INFORMATION: nucleic acid sequence of AJ540 light chain CDR2

<400> SEQUENCE: 34
aaggccagca accggtacac a                                               21

<210> SEQ ID NO 35
<211> LENGTH: 27
<212> TYPE: DNA
<213> ORGANISM: Artificial
<220> FEATURE:
<223> OTHER INFORMATION: nucleic acid sequence of AJ540 light chain CDR3

<400> SEQUENCE: 35
atgcagagca acagcttccc cctgacc                                         27

<210> SEQ ID NO 36
<211> LENGTH: 448
<212> TYPE: PRT
<213> ORGANISM: Artificial
<220> FEATURE:
<223> OTHER INFORMATION: Amino acid sequence of antibody heavy chain

<400> SEQUENCE: 36

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Asn Trp Val Arg Gln Ala Pro Gly Lys Gly Leu Glu Trp Val
        35                  40                  45
```

```
Ala Ser Ile Ser Pro Ser Gly Gly Ser Thr Tyr Tyr Arg Arg Ser Val
    50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
             85                  90                  95
Ala Thr Arg Ala Gly His Asn Tyr Gly Ala Gly Trp Tyr Phe Asp Tyr
            100                 105                 110
Trp Gly Gln Gly Thr Leu Val Thr Val Ser Ser Ala Ser Thr Lys Gly
            115                 120                 125
Pro Ser Val Phe Pro Leu Ala Pro Cys Ser Arg Ser Thr Ser Glu Ser
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Lys Thr Tyr Thr Cys Asn Val
        195                 200                 205
Asp His Lys Pro Ser Asn Thr Lys Val Asp Lys Arg Val Glu Ser Lys
    210                 215                 220
Tyr Gly Pro Pro Cys Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
    275                 280                 285
Ala Lys Thr Lys Pro Arg Glu Glu Gln Phe Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
            325                 330                 335
Thr Ile Ser Lys Ala Lys Gly Gln Pro Arg Glu Pro Gln Val Cys Thr
        340                 345                 350
Leu Pro Pro Ser Gln Glu Glu Met Thr Lys Asn Gln Val Ser Leu Trp
    355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
            405                 410                 415
Ser Arg Trp Gln Glu Gly Asn Val Phe Ser Cys Ser Val Met His Glu
        420                 425                 430
Ala Leu His Asn His Tyr Thr Gln Lys Ser Leu Ser Leu Ser Leu
    435                 440                 445
```

<210> SEQ ID NO 37
<211> LENGTH: 444
<212> TYPE: PRT
<213> ORGANISM: Artificial
<220> FEATURE:
<223> OTHER INFORMATION: Amino acid sequence of antibody heavy chain

<400> SEQUENCE: 37

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Thr Met Thr Ile Asp Lys Ser Thr Gly Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Ser Tyr Gly Tyr Tyr His Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Cys Glu Met Thr Lys Asn Gln Val Ser Leu Ser Cys Ala Val
        355                 360                 365
```

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu
                435                 440

<210> SEQ ID NO 38
<211> LENGTH: 214
<212> TYPE: PRT
<213> ORGANISM: Artificial
<220> FEATURE:
<223> OTHER INFORMATION: Amino acid sequence of antibody light chain

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Asn
            20                  25                  30

Leu Ala Trp Tyr Gln Gln Lys Pro Gly Gln Ala Pro Glu Leu Leu Ile
        35                  40                  45

Tyr Ser Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Leu Ala Thr Tyr Tyr Cys Gln Gln Tyr Tyr Ser Pro Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210
```

METHOD FOR MEASURING REACTIVITY OF FVIII

CROSS-REFERENCE TO RELATED APPLICATIONS

This application is the National Stage of International Application Serial No. PCT/JP2015/076848, filed on Sep. 24, 2015, which claims the benefit of Japanese Application Serial No. 2014-196974, filed on Sep. 26, 2014.

TECHNICAL FIELD

The present invention relates to methods for measuring the reactivity of FVIII in the presence of a substance having an activity of functionally substituting for coagulation factor VIII (FVIII) (for example, methods for measuring FVIII activity or FVIII inhibitor titer). The present invention also relates to kits and such for measuring the reactivity of FVIII in the presence of a substance having an activity of functionally substituting for FVIII.

BACKGROUND ART

Hemophilia is a hemorrhagic disease caused by a congenital defect or dysfunction of FVIII or coagulation factor IX (FIX). The former is called hemophilia A and the latter is called hemophilia B. Both of these genes are located on the X chromosome; and since they are X-chromosome-linked recessive genetic abnormalities, 99% or more of those who develop the disease are men. It is known that the prevalence rate is approximately one in 10,000 male births, and the ratio between hemophilia A and hemophilia B is approximately 5:1.

The main bleeding sites in hemophilia patients include intraarticular, intramuscular, subcutaneous, intraoral, intracranial, digestive tract, intranasal, and such. Among them, repeated intraarticular bleeding can develop into hemophilic arthropathy accompanied by articular disorders and difficulty in walking, which eventually may require joint replacement. Therefore, it is a major factor that lowers the QOL of hemophilia patients.

The severity of hemophilia correlates well with the FVIII activity or FIX activity in blood. Patients with a coagulation factor activity of less than 1% are classified as severe, patients with an activity of 1% or more to less than 5% are classified as moderate, and patients with an activity of 5% or more and less than 40% are classified as mild. Patients with severe symptoms, accounting for approximately half of hemophilia patients, exhibit bleeding symptoms several times a month if they do not receive the later-described preventive replacement therapy, and this frequency is markedly high compared to those of moderately symptomatic patients and mildly symptomatic patients.

In addition to hemophilia and acquired hemophilia, von Willebrand's disease caused by functional abnormality or deficiency of von Willebrand factor (vWF) is known to be a related bleeding abnormality. vWF is not only necessary for platelets to undergo normal adhesion to the subendothelial tissues at lesion sites of vascular walls, but it is also necessary for forming a complex with FVIII and keeping FVIII in the blood at a normal level. In von Willebrand's disease patients, these functions are decreased, leading to hemostasis dysfunction.

For prevention and/or treatment of bleeding in hemophilia patients, blood coagulation factors purified from plasma or those produced by genetic engineering techniques are mainly used. In severe hemophilia patients, maintaining the FVIII activity or FIX activity in the blood at 1% or more by FVIII or FIX replacement therapy are considered to be effective for preventing manifestation of bleeding symptoms (Non-patent Documents 1 and 2). On the other hand, in hemophilia patients, particularly severe hemophilia patients, antibodies against FVIII or FIX which are called inhibitors may be generated. When such inhibitors are generated, the effect of the coagulation factor formulation is blocked by the inhibitors. As a result, neutralization treatment using large amounts of the coagulation factor formulation, or bypass treatment using a complex concentrate or an activated coagulation factor VII formulation (FVIIa formulation) is carried out.

Measurement of the FVIII activity in hemophilia A is carried out mainly by one-stage clotting assay based on activated partial thromboplastin time (APTT) (Non-patent Document 3) and chromogenic assay which is a system reconstructed using a purified coagulation factor (Non-patent Document 4).

Measurement of the FVIII inhibitor titer in hemophilia A is carried out mainly by Bethesda assay or Nijmegen Bethesda assay (Non-patent Documents 5 and 6).

Recently, a bispecific antibody that binds to both FIX and/or activated coagulation factor IX (FIXa) and coagulation factor X (FX) and/or activated blood coagulation factor X (FXa), and substitutes for the cofactor function of FVIII or more specifically, the function of promoting FX activation by FIXa, was found (Non-patent Documents 7 and 8; Patent Documents 1, 2, and 3). The bispecific antibody functionally substitutes for FVIII to improve the decrease in coagulation reaction due to FVIII deficiency or functional abnormality. For example, with respect to thrombin production and APTT which are indicators of the coagulation reaction, the bispecific antibody shortens the APTT of plasma derived from a hemophilia A patient regardless of the presence of an FVIII inhibitor, and increases the production of thrombin. The APTT-shortening effect of the bispecific antibody was remarkable in comparison to FVIII. This is because FVIII in plasma shows cofactor activity only after activation by activated factor X (FXa) or thrombin, whereas the above-mentioned bispecific antibody does not need such activation process, and for that reason, exhibits the cofactor function more quickly.

Furthermore, antibodies against FIXa Fab and against FX Fab of the bispecific antibody were obtained, and the concentrations of the bispecific antibody in plasma samples from animal testing were determined (Non-patent Document 9).

The bispecific antibody substitutes for the cofactor function of FVIII, thus affecting the assay system that measures the reactivity of FVIII itself. For example, when measuring the plasma FVIII activity by APTT-based one-stage clotting assay to diagnose the severity of hemophilia A or to monitor the pharmacological activity of an FVIII formulation in an FVIII formulation-administered patient, the action of promoting the shortening of coagulation time of the bispecific antibody strongly interferes in the presence of the bispecific antibody, which greatly impairs the accuracy of measurement. Furthermore, when determining the plasma FVIII inhibitor titer by APTT-based Bethesda assay, the action of promoting the shortening of coagulation time of the bispecific antibody strongly interferes in the presence of the bispecific antibody, which greatly impairs the accuracy of measurement. That is, in patients administered with the bispecific antibody, the FVIII activity and FVIII inhibitor titer cannot be accurately measured. Therefore, methods that enable measurement of the FVIII activity and FVIII inhibitor titer even in the presence of a bispecific antibody are desired.

CITATION LIST

Non-Patent Documents

Non-patent Document 1: N Engl J Med. 2007; 357(6): 535-44
Non-patent Document 2: Thromb Res. 2011; 127 (suppl1): S14-7
Non-patent Document 3: Thromb Diath Haemorrh. 1962 May 15; 7: 215-28
Non-patent Document 4: Haemostasis. 1989 19: 196-204.
Non-patent Document 5: Thromb Diath Haemorrh. 1975; 34(3): 869-72
Non-patent Document 6: Thromb Haemost. 1995 February; 73(2): 247-51.
Non-patent Document 7: Nat Med. 2012; 18(10): 1570-74
Non-patent Document 8: PLoS One. 2013; 8(2): e57479.
Non-patent Document 9: J Thromb Haemost. 2014; 12(2): 206-13 Supporting Information Patent Documents Patent Document 1: WO2005/035756
Patent Document 2: WO2006/109592
Patent Document 3: WO2012/067176

SUMMARY OF THE INVENTION

Problems to be Solved by the Invention

The present invention relates to methods for measuring the reactivity of FVIII in the presence of a substance having an activity of functionally substituting for FVIII, for example, methods for measuring FVIII activity or FVIII inhibitor titer. Furthermore, an objective of the present invention is to provide kits or the like for measuring the reactivity of FVIII, such as FVIII activity and FVIII inhibitor titer, in the presence of a substance having an activity of functionally substituting for FVIII.

Means for Solving the Problems

To solve the above-mentioned problems, the present inventors produced substances that neutralize the activity of the bispecific antibody and by targeting the test items that measure the reactivity of FVIII, searched for measurement conditions that ensure accuracy even in the presence of the bispecific antibody. As a result, the present inventors found out that by using neutralizing antibodies against the bispecific antibody at appropriate concentrations (for example, concentrations at which the bispecific antibody can be sufficiently neutralized), the FVIII activity in the plasma of hemophilia A patients can be evaluated accurately by APTT-based one-stage clotting assay, and also found out that the FVIII inhibitor titer in the plasma of a hemophilia A patient carrying the FVIII inhibitor can be evaluated accurately by APTT-based Bethesda assay. Furthermore, the present inventors successfully discovered kits containing neutralizing antibodies against the bispecific antibody having an FVIII-substituting activity for use in the measurement. The present invention is based on these findings and provides the following:

[1] a method for measuring reactivity of coagulation factor VIII, wherein the method comprises the step of contacting
(1) a blood-derived sample containing a substance that has an activity of functionally substituting for coagulation factor VIII, with
(2) one or more substances that neutralize the substance having an activity of functionally substituting for coagulation factor VIII;

[2] the method of [1], wherein the substance having an activity of functionally substituting for coagulation factor VIII is a bispecific antibody that binds to coagulation factor IX and/or activated coagulation factor IX and to coagulation factor X and/or activated blood coagulation factor X;

[3] the method of [1] or [2], wherein the bispecific antibody is any one of the antibodies described below, in which a first polypeptide is associated with a third polypeptide and a second polypeptide is associated with a fourth polypeptide:
a bispecific antibody in which the first polypeptide is an H chain consisting of the amino acid sequence of SEQ ID NO: 9, the second polypeptide is an H chain consisting of the amino acid sequence of SEQ ID NO: 11, and the third polypeptide and the fourth polypeptide are common L chains of SEQ ID NO: 10 (Q499-z121/J327-z119/L404-k); or
a bispecific antibody in which the first polypeptide is an H chain consisting of the amino acid sequence of SEQ ID NO: 36, the second polypeptide is an H chain consisting of the amino acid sequence of SEQ ID NO: 37, and the third polypeptide and the fourth polypeptide are common L chains of SEQ ID NO: 38 (Q153-G4k/J142-G4h/L180-k);

[4] the method of any one of [1] to [3], wherein the neutralizing substance is one or more substances selected from the group consisting of peptides, polypeptides, organic compounds, aptamers, and antibodies that neutralize the substance having an activity of functionally substituting for coagulation factor VIII;

[5] the method of any one of [2] to [4], wherein the neutralizing substance is one or more antibodies selected from the group consisting of an antibody that binds to Fab comprising an antigen-binding site that binds to coagulation factor IX, an antibody that binds to Fab comprising an antigen-binding site that binds to activated coagulation factor IX, an antibody that binds to Fab comprising an antigen-binding site that binds to coagulation factor X, an antibody that binds to Fab comprising an antigen-binding site that binds to activated coagulation factor X, and a bispecific antibody that binds to Fab comprising an antigen-binding site that binds to coagulation factor IX and/or activated coagulation factor IX and Fab comprising an antigen-binding site that binds to coagulation factor X and/or activated coagulation factor X;

[6] the method of any one of [1] to [5], wherein the neutralizing substance is one or more combinations selected from the group consisting of the following antibody combinations:
(a) an antibody that binds to Fab comprising an antigen-binding site that binds to coagulation factor IX and an antibody that binds to Fab comprising an antigen-binding site that binds to coagulation factor X;
(b) an antibody that binds to Fab comprising an antigen-binding site that binds to activated coagulation factor IX and an antibody that binds to Fab comprising an antigen-binding site that binds to coagulation factor X;
(c) an antibody that binds to Fab comprising an antigen-binding site that binds to coagulation factor IX and an antibody that binds to Fab comprising an antigen-binding site that binds to activated coagulation factor IX; and (d) an antibody that binds to Fab comprising an antigen-binding site that binds to coagulation factor IX, an antibody that binds to Fab comprising an antigen-binding site that binds to coagulation factor X, and an antibody that binds to Fab comprising an antigen-binding site that binds to activated coagulation factor IX;

[7] the method of any one of [1] to [6], wherein the method for measuring reactivity of coagulation factor VIII is a method for measuring the coagulation factor VIII activity or a method for measuring the coagulation factor VIII inhibitor titer;

[8] a kit for use in the method of any one of [1] to [7], wherein the kit comprises one or more antibodies selected from the group consisting of an antibody that binds to Fab comprising an antigen-binding site that binds to coagulation factor IX, an antibody that binds to Fab comprising an antigen-binding site that binds to activated coagulation factor IX, an antibody that binds to Fab comprising an antigen-binding site that binds to coagulation factor X, an antibody that binds to Fab comprising an antigen-binding site that binds to activated coagulation factor X, and a bispecific antibody that binds to Fab comprising an antigen-binding site that binds to coagulation factor IX and/or activated coagulation factor IX and Fab comprising an antigen-binding site that binds to coagulation factor X and/or activated coagulation factor X;

[9] the kit of [8], wherein the kit comprises one or more combinations selected from the group consisting of the following antibody combinations:

(a) an antibody that binds to Fab comprising an antigen-binding site that binds to coagulation factor IX and an antibody that binds to Fab comprising an antigen-binding site that binds to coagulation factor X;

(b) an antibody that binds to Fab comprising an antigen-binding site that binds to activated coagulation factor IX and an antibody that binds to Fab comprising an antigen-binding site that binds to coagulation factor X;

(c) an antibody that binds to Fab comprising an antigen-binding site that binds to coagulation factor IX and an antibody that binds to Fab comprising an antigen-binding site that binds to activated coagulation factor IX; and (d) an antibody that binds to Fab comprising an antigen-binding site that binds to coagulation factor IX, an antibody that binds to Fab comprising an antigen-binding site that binds to coagulation factor X, and an antibody that binds to Fab comprising an antigen-binding site that binds to activated coagulation factor IX;

[10] a method for diagnosing the disease severity of a patient administered with a substance having an activity of functionally substituting for coagulation factor VIII, wherein the method uses the method of any one of [1] to [7];

[11] a method for diagnosing inhibitor titer in a patient administered with a substance having an activity of functionally substituting for coagulation factor VIII, wherein the method uses the method of any one of [1] to [7];

[12] a method for monitoring pharmacological activity of an FVIII formulation in a patient administered with the FVIII formulation and a substance having an activity of functionally substituting for coagulation factor VIII, wherein the method uses the method of any one of [1] to [7];

[13] the method of any one of [10] to [12], wherein the patient is a patient selected from the group consisting of a hemophilia A patient, an acquired hemophilia A patient, a von Willebrand disease patient, and a patient with hemophilia A in which an inhibitor against blood coagulation factor VIII and/or activated blood coagulation factor VIII emerges;

[14] the kit of [8] or [9], wherein the kit is for diagnosing the disease severity of a patient administered with a substance having an activity of functionally substituting for coagulation factor VIII;

[15] the kit of [8] or [9], wherein the kit is for diagnosing inhibitor titer in a patient administered with a substance having an activity of functionally substituting for coagulation factor VIII;

[16] the kit of [8] or [9], wherein the kit is for monitoring pharmacological activity of an FVIII formulation in a patient administered with the FVIII formulation and a substance having an activity of functionally substituting for coagulation factor VIII; and

[17] the kit of any one of [14] to [16], wherein the patient is a patient selected from the group consisting of a hemophilia A patient, an acquired hemophilia A patient, a von Willebrand disease patient, and with a patient with hemophilia A in which an inhibitor against blood coagulation factor VIII and/or activated blood coagulation factor VIII emerges.

Effects of the Invention

The present invention provides methods that can measure FVIII activity and FVIII inhibitor titer without being influenced by the activity of a substance having an FVIII-substituting activity. A substance having an FVIII-substituting activity includes a bispecific antibody that binds to FIX and/or FIXa and FX and/or FXa.

MODE FOR CARRYING OUT THE INVENTION

Figure 1:
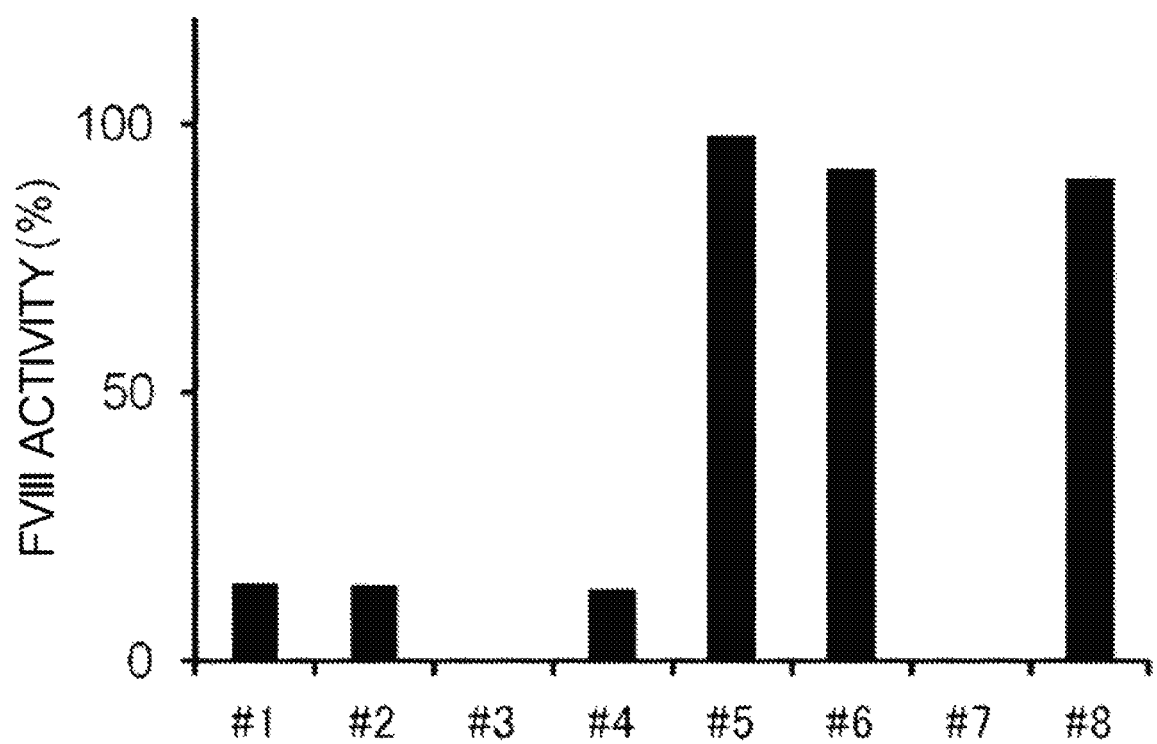
FIG. 1 shows the results of one-stage clotting assay performed under neutralization of the anti-FIXa/FX bispecific antibody using rAQ8-mIgG2b and rAJ540-rbtIgG. When FVIII-deficient plasma containing 10 U/dL or 100 U/dL recombinant FVIII supplemented with an anti-FIXa/FX bispecific antibody, ACE910, was diluted with a buffer (#3 and #7), the FVIII activities were shown to be above the range of the calibration curve. On the other hand, when FVIII-deficient plasma containing 10 U/dL or 100 U/dL recombinant FVIII supplemented with the anti-FIXa/FX bispecific antibody ACE910 was diluted with a buffer containing the two types of antibodies against the anti-FIXa/FX bispecific antibody (#4 and #8), the FVIII activities were shown to be similar to those of the groups without addition of the anti-FIXa/FX bispecific antibody (#1 and #5). When FVIII-deficient plasma containing 10 U/dL or 100 U/dL recombinant FVIII was diluted with a buffer containing only the two types of antibodies against the anti-FIXa/FX bispecific antibody (#2 and #6), the FVIII activities were shown to be similar to those of the groups without addition of the anti-FIXa/FX bispecific antibody (#1 and #5).

The method for measuring FVIII activity of the present invention comprises the step of contacting (1) and (2) described below. Otherwise, the method can be carried out according to methods generally used for measuring FVIII activity. Details will be explained in the Examples as well.
(1) a blood-derived sample containing a substance having an activity of functionally substituting for FVIII
(2) a substance that neutralizes the substance having an activity of functionally substituting for FVIII
Methods for Measuring FVIII Activity The FVIII activity measurement methods that are generally used and known to those skilled in the art can be used, and for example, one can use a one-stage clotting assay (Casillas et al., (1971) Coagulation 4: 107-11) that uses factor VIII-deficient plasma (Sysmex, Kobe, Japan), which is based on coagulation time (aPTT measurements). One-stage clotting assay is carried out, for example, by the following method. Three solutions, 50 µL of ten-fold diluted test plasma, 50 µL of FVIII-deficient plasma, and 50 µL of an APTT reagent are mixed; and this is incubated at 37° C. for five minutes, followed by addition of 50 µL of a calcium solution to initiate the coagulation reaction, and then the time to coagulation is measured. Furthermore, instead of the test plasma, serially diluted samples of normal plasma (FVIII activity in a ten-fold diluted normal plasma is specified as 100%) are measured, and a calibration curve is produced by plotting the FVIII activity on the horizontal axis and coagulation time on the vertical axis. The coagulation time of the test plasma is converted to FVIII activity using the calibration curve, and FVIII activity in the test plasma is calculated. Herein, unless stated otherwise, the phrase "measurement of FVIII activity" is used as a phrase that may include "measurement of activated coagulation factor VIII (FVIIIa) activity".

In addition to one-stage clotting assay, thrombin generation assay (TGA), measurement methods that use rotation thromboelastometry, FVIII chromogenic assay, coagulation waveform analysis, thrombin and activated factor X production assay, and such may be used as the method for measuring FVIII activity. The method for measuring FVIII inhibitor titer of the present invention includes the step of contacting (1) and (2) described below. Otherwise, the method can be carried out according to generally used methods for measuring FVIII inhibitor titer. Details will be explained in the Examples as well.
(1) a blood-derived sample containing a substance having an activity of functionally substituting for FVIII
(2) a substance that neutralizes the substance having an activity of functionally substituting for FVIII
Methods for Measuring FVIII Inhibitor Titer The FVIII inhibitor titer measurement methods that are generally used and known to those skilled in the art can be used, and for example, one can use Bethesda assay (Kasper et al., (1975) Thrombos Diath Haemorrh 34: 869-872), ELISA method, and Nijmegen Bethesda assay (Nijmegen modification assay) (Verbruggen et al., (1995) Thromb Haemost 73: 247-251). Bethesda assay is carried out, for example, by the following method. A solution produced by mixing equal amounts of normal plasma and test plasma is incubated at 37° C. for two hours, and then the residual factor VIII activity in normal plasma is measured by one-stage clotting assay based on activated partial thromboplastin time (APTT). The action of inhibiting 50% of the factor VIII activity in normal plasma is specified as 1 Bethesda (1BU), and therefore the FVIII inhibitor titer is calculated in units of Bethesda. When the FVIII inhibitor titer in the test plasma is high and the residual FVIII activity does not lie within the range of 25% to 75%, test plasma suitably diluted with a buffer is used to recalculate the Bethesda units, and subsequently, the value is multiplied by the dilution ratio to calculate the FVIII inhibitor titer in the test plasma.

FVIII

FVIII is one of a series of molecules involved in blood coagulation, which demonstrates cofactor activity when it is activated by thrombin or FXa and promotes the FX activation reaction by FIXa.

FVIII Inhibitor

The FVIII inhibitor is an isoantibody against foreign FVIII and is emerged in 20% to 30% of hemophilia A patients. An individual who is originally normal may produce autoantibodies against FVIII posteriori. Generally, most FVIII inhibitor isoantibodies and autoantibodies function as anti-FVIII neutralizing antibodies, and decrease or eliminate FVIII activity.

Activity of Substituting for FVIII

A substance having an activity of functionally substituting for FVIII of the present invention can be rephrased as a substance having an FVIII-like activity. In the present invention, the phrase "functionally substitute/substituting for FVIII" means that FX activation by FIXa is promoted (FXa generation by FIXa is promoted). More specifically, in the present invention, the phrase "functionally substitute/substituting for FVIII" means recognizing FIX and/or FIXa, and FX and/or FXa, and promoting activation of FX by FIXa (promoting FXa generation by FIXa). The activity of promoting FXa generation can be evaluated using, for example, a measurement system comprising FIXa, FX, synthetic substrate S-2222 (synthetic substrate of FXa), and phospholipids. Such measurement system shows correlation between the severity of the disease and clinical symptoms in hemophilia A cases (Rosen S, Andersson M, Blombäck M et al. Clinical applications of a chromogenic substrate method for determination of FVIII activity. Thromb Haemost 1985; 54: 811-23).

A preferred embodiment of a substance having an activity of functionally substituting for FVIII of the present invention includes, for example, a bispecific antibody that binds to FIX and/or FIXa, and to FX and/or FXa. Such an antibody can be obtained according to methods described, for example, in WO2005/035756, WO2006/109592, and WO2012/067176. The bispecific antibody of the present invention includes antibodies described in these documents.

A preferred bispecific antibody includes, for example, ACE910 (Q499-z121/J327-z119/L404-k) (a bispecific antibody in which the H chain consisting of the amino acid sequence of SEQ ID NO: 9 and the L chain of SEQ ID NO: 10 are associated, and the H chain consisting of the amino acid sequence of SEQ ID NO: 11 and the L chain of SEQ ID NO: 10 are associated) and hBS23 (Q153-G4k/J142-G4h/L180-k) (a bispecific antibody in which the H chain consisting of the amino acid sequence of SEQ ID NO: 36 and the L chain of SEQ ID NO: 38 are associated, and the H chain consisting of the amino acid sequence of SEQ ID NO: 37 and the L chain of SEQ ID NO: 38 are associated), which are bispecific antibodies described in a patent document (WO2012/067176).

Neutralization

"Neutralization" in a substance that neutralizes the substance having an activity of functionally substituting for FVIII in the present invention refers to, for example, complete or partial inhibition of the activity of functionally substituting for FVIII of a substance that has an activity of functionally substituting for FVIII. For example, when the substance having the activity of functionally substituting for FVIII is an antibody, complete or partial inhibition of the activity of functionally substituting for FVIII may be accomplished by completely or partially inhibiting binding of the antibody to the antigen, but is not limited thereto Neutralizing Substances The term "substance" of the neutralizing substance in the substance that neutralizes the substance having an activity of functionally substituting for FVIII in the present invention refers to, for example, peptides, polypeptides, organic compounds, aptamers, antibodies, and such that bind to the substance having an activity of functionally substituting for FVIII.

A plurality of neutralizing substances can be used in combination, and for example, antibodies and aptamers can be used in combination.

Polypeptides

Polypeptides in the present invention normally refer to proteins and peptides having a length of approximately ten amino acids or longer. Generally, they are biologically derived polypeptides, but are not particularly limited to such polypeptides, and may be, for example, polypeptides comprising an artificially designed sequence. Furthermore, they may be any native polypeptides, or synthetic polypeptides, recombinant polypeptides, or such. Additionally, the fragments of the above-mentioned polypeptide are also included in the polypeptides of the present invention.

Organic Compounds

Organic compounds in the present invention are, for example, low-molecular-weight compounds, preferably with a molecular weight of 1000 or less.

Aptamers

The term "aptamer" refers to a nucleic acid molecule that binds specifically to a target molecule such as a polypeptide. For example, aptamers of the present invention can be RNA aptamers capable of binding specifically to substances having an FVIII-substituting activity. Production and therapeutic use of aptamers are well established in this field. For example, aptamers can be obtained by using the SELEX method (see U.S. Pat. Nos. 5,475,096, 5,580,737, 5,567,588, 5,707,796, 5,763,177, 6,699,843, and such).

Antibodies

When the substance having an activity of functionally substituting for FVIII is a bispecific antibody that binds to FIX and/or FIXa and to FX and/or FXa, examples of antibodies that bind to the substance having an activity of functionally substituting for FVIII include antibodies selected from the group consisting of antibodies that bind to Fab containing an antigen-binding site that binds to FIX, antibodies that bind to Fab containing an antigen-binding site that binds to FIXa, antibodies that bind to Fab containing an antigen-binding site that binds to FX, antibodies that bind to Fab containing an antigen-binding site that binds to FXa, and bispecific antibodies that bind to Fab containing an antigen-binding site that binds to FIX and/or FIXa and to Fab containing an antigen-binding site that binds to FX and/or FXa. The above-mentioned antibodies can be used separately or in multi-combinations. For example, it is possible to use multiple antibodies that bind to Fab containing an antigen-binding site that binds to one type of antigen, for example, multiple types of antibodies that bind to Fab containing an antigen-binding site that binds to FIX. For example, when the substance having an activity of functionally substituting for FVIII is a bispecific antibody that binds to FIX and/or FIXa and to FX and/or FXa, the following antibody combinations can be used:

(a) an antibody that binds to Fab containing an antigen-binding site that binds to FIX and an antibody that binds to Fab containing an antigen-binding site that binds to FX;

(b) an antibody that binds to Fab containing an antigen-binding site that binds to FIXa and an antibody that binds to Fab containing an antigen-binding site that binds to FX;

(c) an antibody that binds to Fab containing an antigen-binding site that binds to FIX and an antibody that binds to Fab containing an antigen-binding site that binds to FIXa; and (d) an antibody that binds to Fab containing an antigen-binding site that binds to FIX, an antibody that binds to Fab containing an antigen-binding site that binds to FX, and an antibody that binds to Fab containing an antigen-binding site that binds to FIXa.

An example of an antibody that binds to Fab containing an antigen-binding site that binds to FIX and/or FIXa includes the AQ8, AQ1, and AQ512 antibodies. The nucleotide sequences of the variable regions and the amino acid sequences predicted therefrom were analyzed by GENETYX Ver. 9 (GENETYX CORPORATION).

The amino acid sequence and the nucleotide sequence of the H chain variable region of AQ8 are indicated by the following SEQ ID NOs:
 amino acid sequence: SEQ ID NO: 1; and
 nucleotide sequence: SEQ ID NO: 5.

The amino acid sequence and the nucleotide sequence of the L chain variable region of AQ8 are indicated by the following SEQ ID NOs:
 amino acid sequence: SEQ ID NO: 2; and
 nucleotide sequence: SEQ ID NO: 6.

The amino acid sequences and the nucleotide sequences of the H-chain CDRs 1 to 3 of AQ8 are indicated by the following SEQ ID NOs:
 CDR1 amino acid sequence: SEQ ID NO: 12;
 CDR2 amino acid sequence: SEQ ID NO: 13;
 CDR3 amino acid sequence: SEQ ID NO: 14;
 CDR1 nucleotide sequence: SEQ ID NO: 15;
 CDR2 nucleotide sequence: SEQ ID NO: 16; and
 CDR3 nucleotide sequence: SEQ ID NO: 17.

The amino acid sequences and the nucleotide sequences of the L-chain CDRs 1 to 3 of AQ8 are indicated by the following SEQ ID NOs:
 CDR1 amino acid sequence: SEQ ID NO: 18;
 CDR2 amino acid sequence: SEQ ID NO: 19;
 CDR3 amino acid sequence: SEQ ID NO: 20;
 CDR1 nucleotide sequence: SEQ ID NO: 21;
 CDR2 nucleotide sequence: SEQ ID NO: 22; and
 CDR3 nucleotide sequence: SEQ ID NO: 23.

An example of an antibody that binds to Fab containing an antigen-binding site that binds to FX and/or FXa includes the AJ540, AJ541, AJ522, AJ114, and AJ521 antibodies. The nucleotide sequences of the variable regions and the amino acid sequences predicted therefrom were analyzed by GENETYX Ver. 9 (GENETYX CORPORATION).

The amino acid sequence and the nucleotide sequence of the H chain variable region of AJ540 are indicated by the following SEQ ID NOs:
 amino acid sequence: SEQ ID NO: 3; and
 nucleotide sequence: SEQ ID NO: 7.

The amino acid sequence and the nucleotide sequence of the L chain variable region of AJ540 are indicated by the following SEQ ID NOs:
 amino acid sequence: SEQ ID NO: 4; and
 nucleotide sequence: SEQ ID NO: 8.

The amino acid sequences and the nucleotide sequences of the H-chain CDRs 1 to 3 of AJ540 are indicated by the following SEQ ID NOs:
 CDR1 amino acid sequence: SEQ ID NO: 24;
 CDR2 amino acid sequence: SEQ ID NO: 25;
 CDR3 amino acid sequence: SEQ ID NO: 26;
 CDR1 nucleotide sequence: SEQ ID NO: 27;
 CDR2 nucleotide sequence: SEQ ID NO: 28; and
 CDR3 nucleotide sequence: SEQ ID NO: 29.

The amino acid sequences and the nucleotide sequences of the L-chain CDRs 1 to 3 of AJ540 are indicated by the following SEQ ID NOs:
 CDR1 amino acid sequence: SEQ ID NO: 30;
 CDR2 amino acid sequence: SEQ ID NO: 31;
 CDR3 amino acid sequence: SEQ ID NO: 32;
 CDR1 nucleotide sequence: SEQ ID NO: 33;
 CDR2 nucleotide sequence: SEQ ID NO: 34; and
 CDR3 nucleotide sequence: SEQ ID NO: 35.

The term "antibody" is used in the broadest sense, and may be monoclonal antibodies, polyclonal antibodies, dimers, multimers, multispecific antibodies (for example, bispecific antibodies), antibody derivatives, and modified antibody products (Miller K et al. J Immunol. 2003, 170(9), 4854-61) as long as they display a desired biological activity. The antibodies may be mouse antibodies, human antibodies, humanized antibodies, chimeric antibodies, or those derived from another species, or they may be artificially synthesized antibodies. The antibodies disclosed herein can be of any type (for example, IgG, IgE, IgM, IgD, and IgA), class (for example, IgG1, IgG2, IgG3, IgG4, IgA1 and IgA2) or subclass of immunoglobulin molecules. The immunoglobulins can be derived from any species (for example, human, mouse, or rabbit). The terms "antibody", "immune globulin" and "immunoglobulin" are used interchangeably in a broad sense.

The term "antibody derivative" includes a portion of an antibody, preferably an antibody variable region, or at least an antigen-binding region of an antibody. Antibody derivatives include, for example, Fab, Fab', F(ab')2, Fv fragments, linear antibodies, and single-chain antibodies (scFv), sc(Fv)$_2$, Fab$_3$, domain antibodies (dAb) (WO2004/058821, WO2003/002609), diabodies, triabodies, tetrabodies, minibodies, and multispecific antibodies formed from antibody derivatives, but are not limited thereto. Here, "Fab" is constructed from a single light chain and the CH1 domain and variable region of a single heavy chain. Furthermore, "Fv" is the smallest antibody derivative, and includes a complete antigen-recognizing region and an antigen-binding region. The antibody derivative may be, for example, a fusion between an IgG antibody and Fc. For example, one can refer to Example 2 in U.S. Pat. No. 5,641,870 specification; Zapata G et al. Protein Eng. 1995, 8(10), 1057-1062; Olafsen T et al. Protein Eng. Design & Sel. 2004, 17(4): 315-323; Holliger P et al. Nat. Biotechnol. 2005, 23(9): 1126-36; Fischer N et al. Pathobiology. 2007, 74(1): 3-14; Shen J et al. J Immunol Methods. 2007, 318, 65-74; and Wu et al. Nat Biotechnol. 2007, 25(11), 1290-7.

Examples of modified antibody products may include antibodies linked to various molecules such as polyethylene glycol (PEG). Antibodies of the present invention include such modified antibody products. The substance to be linked is not limited in the modified antibody products of the present invention. To yield such modified antibody products, chemical modifications can be made to the obtained antibodies. Such methods are already established in this field.

"Bispecific" antibodies refer to antibodies having variable regions that recognize different epitopes, where the regions are within the same antibody molecule. Bispecific antibodies may be antibodies that recognize two or more different antigens or antibodies that recognize two or more different epitopes on the same antigen. Bispecific antibodies may include not only whole antibodies but antibody derivatives. Antibodies of the present invention also include bispecific antibodies. Herein, anti-FIXa/FX bispecific antibody and bispecific antibody that binds to FIXa and FX are used synonymously.

Methods for Producing Genetically Engineered Antibodies

Recombinant antibodies produced by using genetic engineering techniques can be used as the antibodies. Recombinant antibodies can be obtained by cloning DNAs encoding the antibodies from hybridomas or antibody-producing cells such as sensitized lymphocytes that produce antibodies, inserting them into vectors, and then introducing them into hosts (host cells) to produce the antibodies.

The antibodies include human antibodies, mouse antibodies, and rat antibodies, and their origin is not limited. They may also be genetically modified antibodies such as chimeric antibodies and humanized antibodies.

Methods for obtaining human antibodies are known. For example, transgenic animals carrying the entire repertoire of human antibody genes can be immunized with antigens of interest to obtain human antibodies of interest (see International Publication WO 93/12227, WO 92/03918, WO 94/02602, WO 94/25585, WO 96/34096, and WO 96/33735).

Genetically modified antibodies can be produced using known methods. Specifically, for example, chimeric antibodies comprise H chain and L chain variable regions of an immunized animal antibody, and H chain and L chain constant regions of a human antibody. Chimeric antibodies can be obtained by linking DNAs encoding the variable regions of the antibody derived from the immunized animal, with DNAs encoding the constant regions of a human antibody, inserting this into an expression vector, and then introducing it into host to produce the antibodies.

Humanized antibodies are modified antibodies that are also referred to as reshaped human antibodies. A humanized antibody is constructed by transferring the CDRs of an antibody derived from an immunized animal to the complementarity determining regions of a human antibody. Conventional genetic recombination techniques for such purposes are known (see European Patent Application Publication No. EP 239400; International Publication No. WO 96/02576; Sato K et al., Cancer Research 1993, 53: 851-856; International Publication No. WO 99/51743).

Bispecific antibodies are antibodies that have specificity to two different antigens.

While bispecific antibodies are not limited to those of the IgG type, for example, IgG-type bispecific antibodies can be secreted from a hybrid hybridoma (quadroma) produced by fusing two types of hybridomas that produce IgG antibodies (Milstein C. et al., Nature 1983, 305: 537-540). They can also be secreted by introducing the L chain and H chain genes constituting the two types of IgGs of interest, a total of four types of genes, into cells to co-express the genes.

In this case, by introducing suitable amino acid substitutions to the CH3 regions of the H chains, IgGs having a heterogeneous combination of H chains can be preferentially secreted (Ridgway J B et al. Protein Engineering 1996, 9: 617-621; Merchant A M et al. Nature Biotechnology 1998, 16: 677-681; WO 2006/106905; Davis J H et al. Protein Eng Des Sel. 2010, 4: 195-202).

Regarding the L chains, since the diversity of L chain variable regions is lower than that of H chain variable regions, one can expect to obtain common L chain that can confer binding ability to both H chains. The antibodies of the present invention may be antibodies comprising common L chains. Bispecific IgGs can be efficiently expressed by introducing the gene of the common L chain and both H chains into cells.

Epitopes

Antibodies which are an embodiment of substances that neutralize the substance having an activity of functionally substituting for FVIII of in present invention include antibodies that bind to an epitope overlapping with an epitope bound by the antibodies described above, and preferably antibodies that bind to the same epitope.

Whether an antibody recognizes the same epitope as or an epitope overlapping with an epitope that is recognized by another antibody can be confirmed by competition between the two antibodies against the epitope. Competition between the antibodies can be evaluated by competitive binding assays using means such as enzyme-linked immunosorbent assay (ELISA), fluorescence energy transfer method (FRET), and fluorometric microvolume assay technology (FMAT (Registered trademark)). The amount of antibodies bound to an antigen indirectly correlate with the binding ability of candidate competitor antibodies (test antibodies) that competitively bind to the same or overlapping epitope. In other words, as the amount of or the affinity of test antibodies against the same or overlapping epitope increases, the amount of antibodies bound to the antigen decreases, and the amount of test antibodies bound to the antigen increases. Specifically, the appropriately labeled antibodies and test antibodies are simultaneously added to the antigens, and then the bound antibodies are detected using the label. The amount of the antibodies bound to the antigen can be easily determined by labeling the antibodies in advance. This label is not particularly limited, and the labeling method is selected according to the assay technique used. Specific examples of the labeling method include fluorescent labeling, radiolabeling, and enzyme labeling.

Herein, the "antibody that binds to the overlapping epitope" or "antibody that binds to the same epitope" refers to a test antibody that can reduce the amount of binding of the labeled antibody by at least 50% at a concentration that is usually 100 times higher, preferably 80 times higher, more preferably 50 times higher, even more preferably 30 times higher, and still more preferably 10 times higher than a concentration of the non-labeled antibody at which binding of the non-labeled antibody reduces the amount of binding of the labeled antibody by 50% ($IC_{50}$). The epitope recognized by the antibody can be analyzed by methods known to those skilled in the art, and for example, it can be performed by Western blotting and such.

Antibody Production Methods

Antibodies of the present invention can be produced by methods known to those skilled in the art. Specifically, DNA encoding the antibody of interest is inserted into an expression vector. Insertion into an expression vector is carried out such that the expression will take place under the control of expression regulatory regions such as enhancers and promoters. Next, host cells are transformed using this expression vector to express the antibodies. Appropriate combinations of the host and expression vector can be used in this step.

Examples of the vectors include M13 series vectors, pUC series vectors, pBR322, pBluescript, and pCR-Script. In addition to these vectors, for example, pGEM-T, pDIRECT, or pT7 can also be used for the purpose of cDNA subcloning and excision.

Particularly, expression vectors are useful for using the vectors for the purpose of producing the antibody. For example, when the host is *E. coli* such as JM109, DH5α, HB101, or XL1-Blue, the expression vectors indispensably have a promoter that permits efficient expression in *E. coli*, for example, lacZ promoter (Ward et al., Nature (1989) 341, 544-546; and FASEB J (1992) 6, 2422-2427), araB promoter (Better et al., Science (1988) 240, 1041-1043), or T7 promoter. Examples of such vectors include the vectors mentioned above as well as pGEX-5X-1 (manufactured by Pharmacia), "QIAexpress system" (manufactured by QIAGEN), pEGFP, and pET (in this case, the host is preferably BL21 expressing T7 RNA polymerase).

The vectors may contain a signal sequence for polypeptide secretion. In the case of production in the periplasm of *E. coli*, pelB signal sequence (Lei, S. P. et al., J. Bacteriol. (1987) 169, 4397) can be used as the signal sequence for polypeptide secretion. The vectors can be transferred to the host cells using, for example, calcium chloride methods or electroporation methods.

In addition to the *E. coli* expression vectors, examples of the vectors for producing the antibody of the present invention include mammal-derived expression vectors (e.g., pcDNA3 (manufactured by Invitrogen Corp.), pEGF-BOS (Nucleic Acids. Res. 1990, 18(17), p 5322), pEF, and pCDM8), insect cell-derived expression vectors (e.g., "Bac-to-BAC baculovirus expression system" (manufactured by GIBCO BRL), and pBacPAK8), plant-derived expression vectors (e.g., pMH1 and pMH2), animal virus-derived expression vectors (e.g., pHSV, pMV, and pAdexLcw), retrovirus-derived expression vectors (e.g., pZIPneo), yeast-derived expression vectors (e.g., "*Pichia* Expression Kit" (manufactured by Invitrogen Corp.), pNV11, and SP-Q01), and *Bacillus subtilis*-derived expression vectors (e.g., pPL608 and pKTH50).

For the purpose of expression in animal cells such as CHO cells, COS cells, or NIH3T3 cells, the vectors indispensably have a promoter necessary for intracellular expression, for example, SV40 promoter (Mulligan et al., Nature (1979) 277, 108), MMTV-LTR promoter, EF1α promoter (Mizushima et al., Nucleic Acids Res (1990) 18, 5322), CAG promoter (Gene (1991) 108, 193), or CMV promoter and, more preferably, have a gene for screening for transformed cells (e.g., a drug resistance gene that can work as a marker by a drug (neomycin, G418, etc.)). Examples of the vectors having such properties include pMAM, pDR2, pBK-RSV, pBK-CMV, pOPRSV, and pOP13.

An exemplary method intended to stably express the gene and increase the number of intracellular gene copies involves transfecting CHO cells deficient in nucleic acid synthesis pathway with vectors having a DHFR gene serving as a complement thereto (e.g., pCHOI) and using methotrexate (MTX) in the gene amplification. An exemplary method intended to transiently express the gene involves using COS cells having a gene which expresses an SV40 T antigen on their chromosomes to transform the cells with vectors having a replication origin of SV40 (pcD, etc.). Also, a replication origin derived from polyomavirus, adenovirus, bovine papillomavirus (BPV), or the like may be used. The expression vectors for increasing the number of gene copies in a host cell system can additionally contain a selection marker such as an aminoglycoside transferase (APH) gene, a thymidine kinase (TK) gene, an *E. coli* xanthine guanine phosphoribosyltransferase (Ecogpt) gene, or a dihydrofolate reductase (dhfr) gene.

The antibodies of the present invention obtained by the methods described above can be isolated from inside host cells or from outside of the cells (the medium, or such), and purified to practically pure and homogeneous antibodies. The antibodies can be separated and purified by methods routinely used for separating and purifying antibodies, and the type of method is not limited. For example, the antibodies can be separated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectrofocusing, dialysis, recrystallization, and such.

The chromatographies include, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). The chromatographic methods described above can be conducted using liquid-chromatography, for example, HPLC and FPLC. Columns used for affinity chromatography include protein A columns and protein G columns. Columns using protein A include, for example, Hyper D, POROS, and Sepharose FF (GE Amersham Biosciences). The present invention includes antibodies that are highly purified using these purification methods.

The obtained antibodies can be purified to homogeneity. Separation and purification of the antibodies can be performed using separation and purification methods generally used for protein separation and purification. For example, the antibodies can be separated and purified by appropriately selecting and combining column chromatography such as affinity chromatography, filtration, ultrafiltration, salting-out, dialysis, SDS-polyacrylamide gel electrophoresis, isoelectric focusing, and such, without limitation (Antibodies: A Laboratory Manual. Ed Harlow and David Lane, Cold Spring Harbor Laboratory, 1988). Columns used for affinity chromatography include, for example, protein A columns and protein G columns.

Methods for Obtaining Samples

In the present invention, blood-derived samples are preferably blood-derived samples collected from a test subject. Such blood-derived samples can be obtained from test subjects administered with a substance having an FVIII-substituting activity. A test subject includes, for example, a patient with hemorrhagic symptoms at any part in the body (hemorrhagic disease patient). The main bleeding sites are intraarticular, intramuscular, subcutaneous, intraoral, intracranial, digestive tract, intranasal, and such, but are not limited thereto. The hemorrhagic disease patient is preferably a patient with hemorrhagic disease caused by decrease or deficiency in an FVIII activity and/or FVIIIa activity. The patient with hemorrhagic disease caused by decrease or deficiency in the FVIII activity and/or FVIIIa activity is a patient with hemorrhagic symptoms, and examples include patients with a priori or posteriori decrease or deficiency in either or both of the FVIII activity and FVIIIa activity. Decrease in the activities of FVIII and FVIIIa means that in comparison to those of healthy individuals, these activities are preferably less than 40% (for example, less than 40%, less than 30%, less than 20%, or less than 10%), more preferably less than 10% (for example, less than 10%, less than 9%, less than 8%, less than 7%, or less than 6%), even more preferably less than 5% (for example, less than 5%, less than 4%, less than 3%, or less than 2%), and particularly preferably less than 1% in a patient, without being limited thereto.

More specifically, examples of such diseases include diseases selected from among hemophilia (hemophilia A and hemophilia B), acquired hemophilia, and von Willebrand's disease caused by functional abnormality or deficiency of von Willebrand factor (vWF), but are not limited thereto. Blood-derived samples include serum, plasma, or whole blood. In the present invention, use of plasma samples is preferred. Methods for obtaining blood-derived samples from test subjects are well known to those skilled in the art.

Kits

Various types of reagents such as buffers required for the method for measuring the reactivity of FVIII of the present invention can be packaged in advance and provided as a kit. The kit of the present invention may include in addition to the buffer, plasma samples isolated from a human whose FVIII activity and FIX activity in the blood are normal, a substance having an FVIII-substituting activity, and anything that can be used in FVIII activity measurement, or anything that can be used in FVIII inhibitor titer measurement. Furthermore, the various types of reagents included in the kit can be made into a powder or liquid form according to their mode of use. Furthermore, they can be stored in appropriate containers and used when suitable.

The disease severity of a patient administered with the substance having an activity of functionally substituting for FVIII, for example, can be diagnosed by using the method of the present invention. Reactivity of FVIII can be measured using the method of this invention, and the disease severity and/or inhibitor titer for the patient can be diagnosed/assessed based on the measurement results. The diagnosis and assessment methods can be performed by methods known to those skilled in the art.

The pharmacological activity of an FVIII formulation in patients administered with the FVIII formulation and a substance having an activity of functionally substituting for FVIII, for example, can be monitored by using the methods of the present invention. Monitoring can be carried out by methods known to those skilled in the art.

The kit of the present invention can be used as a kit for diagnosing the disease severity of a patient administered with a substance having an activity of functionally substituting for FVIII. Reactivity of FVIII can be measured using the kit of this invention, and the disease severity of the patient can be diagnosed/assessed based on the measurement results. The diagnosis and assessment methods can be performed by methods known to those skilled in the art.

The kit of the present invention can be used, for example, as a kit for monitoring the pharmacological activity of an FVIII formulation in a patient administered with the FVIII formulation and a substance having an activity of functionally substituting for FVIII. Monitoring can be carried out by methods known to those skilled in the art.

For example, one may use a method for treating a patient, which comprises the steps of:
(a) administering a first dose of a substance having an activity of functionally substituting for FVIII;
(b) monitoring the reactivity of FVIII in the patient;
(c) determining a second dose of the substance having an activity of functionally substituting for FVIII based on the observed reactivity of FVIII; and
(d) administering to the patient the second dose of the substance having an activity of functionally substituting for FVIII.

Furthermore, one may use, for example, a method for treating a patient, which comprises the steps of:
(a) administering a substance having an activity of functionally substituting for FVIII following a first administration interval;
(b) monitoring the reactivity of FVIII in the patient;
(c) determining a second administration interval for the substance having an activity of functionally substituting for FVIII based on the observed reactivity of FVIII; and
(d) administering to the patient the substance having an activity of functionally substituting for FVIII following the second administration interval.

One may also use, for example, a method for treating a patient, which comprises monitoring the reactivity of FVIII, and changing the administration dose and/or the administration interval of the substance having an activity of functionally substituting for coagulation factor VIII depending on the reactivity of FVIII.

The substance having an activity of functionally substituting for FVIII is preferably a bispecific antibody that binds to FIX and/or FIXa and to FX and/or FXa. It is more preferably the antibody described below, which is a bispecific antibody in which a first polypeptide is associated with a third polypeptide and a second polypeptide is associated with a fourth polypeptide bispecific antibody in which the first polypeptide is an H chain consisting of the amino acid sequence of SEQ ID NO: 9, the second polypeptide is an H chain consisting of the amino acid sequence of SEQ ID NO: 11, and the third polypeptide and the fourth polypeptide are common L chains of SEQ ID NO: 10 (Q499-z121/J327-z119/L404-k), or bispecific antibody in which the first polypeptide is an H chain consisting of the amino acid sequence of SEQ ID NO: 36, the second polypeptide is an H chain consisting of the amino acid sequence of SEQ ID NO: 37, and the third polypeptide and the fourth polypeptide are common L chains of SEQ ID NO: 38 (Q153-G4k/J142-G4h/L180-k).

The dose is, for example, 0.001 mg/kg to 100 mg/kg for the aforementioned bispecific antibody. It is preferably approximately 0.001 mg/kg, approximately 0.003 mg/kg, approximately 0.005 mg/kg, approximately 0.01 mg/kg, approximately 0.03 mg/kg, approximately 0.05 mg/kg, approximately 0.1 mg/kg, approximately 0.3 mg/kg, approximately 0.5 mg/kg, approximately 1 mg/kg, approximately 3 mg/kg, approximately 5 mg/kg, approximately 10 mg/kg, approximately 20 mg/kg, approximately 30 mg/kg, approximately 40 mg/kg, approximately 50 mg/kg, approximately 60 mg/kg, approximately 70 mg/kg, approximately 80 mg/kg, approximately 90 mg/kg, and approximately 100 mg/kg. The doses before and after the monitoring step may be the same or different. In the case of the aforementioned bispecific antibody, the administration interval is, for example, at least one day or more. The interval is preferably 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 1 month, 2 months, 3 months, 4 months, 5 months, 6 months, 7 months, 8 months, 9 months, 10 months, 11 months, or 1 year. The dose intervals before and after the monitoring step may be the same or different.

The target patients for the methods or kits of the present invention are, for example, hemophilia A patients, acquired hemophilia A patients, von Willebrand disease patients, and hemophilia A patients with emergence of an inhibitor against FVIII and/or FVIIIa.

As used herein, embodiments represented by the expression "comprising . . . " include embodiments represented by the expression "essentially consisting of . . . " and embodiments represented by the expression "consisting of . . . ".

All patents and reference documents explicitly cited herein are incorporated by reference into this description in their entirety.

The present invention will be further illustrated by the Examples, but it is not to be construed as being limited thereto.

EXAMPLES

Herein below, the present invention will be specifically described by the Examples, but it is not to be construed as being limited thereto.

Example 1 Production of Antibodies Against the Anti-FIXa/FX Bispecific Antibody and Sequence Determination of the Variable Region An attempt was made to generate antibodies against ACE910 (Q499-z121/J327-z119/L404-k) (bispecific antibody in which an H chain consisting of the amino acid sequence of SEQ ID NO: 9 is associated with the L chain of SEQ ID NO: 10, and an H chain consisting of the amino acid sequence of SEQ ID NO: 11 is associated with the L chain of SEQ ID NO: 10), which is a bispecific antibody described in the Patent Document 3 (WO 2012/067176). Gene recombination techniques and pepsin digestion were used to produce F(ab')2 composed from the respective Fabs of the anti-FIXa side and the anti-FX side.

Mice and rats were immunized with anti-FIXa-F(ab')2 or anti-FX-F(ab')2. Cells obtained from the spleen removed from the mice or rats or from rat lymph nodes were subjected to cell fusion with mouse myeloma cells by following general methods to produce the hybridomas. The culture supernatants of the hybridomas were evaluated by ELISA which detects the binding of ACE910 to the anti-FIXa-arm or the anti-FX-arm, and ultimately, mouse antibodies, AQ8 and AQ1, and rat antibody, AQ512, which bind only to the anti-FIXa-arm but not to the anti-FX-arm of ACE910, and rat antibodies, AJ540, AJ114, AJ521, AJ522, and AJ541, which bind only to the anti-FX-arm but not to the anti-FIXa-arm of ACE910 were selected. In addition, the nucleotide sequences of the variable regions of the AQ8 antibody or the AJ540 antibody were analyzed. The nucleotide sequences of the variable regions of AQ8 and AJ540, and amino acid sequences predicted therefrom were analyzed using GENETYX Ver.9 (GENETYX CORPORATION).

Example 2 Production of Expression Vectors for Recombinant Mouse Antibody AQ8 and Recombinant Rat-Rabbit Chimeric Antibody AJ540

Recombinant mouse antibody AQ8 was prepared by combining the variable region sequences of the AQ8 antibody obtained in Example 1 with a known mouse IgG2b constant region sequences (heavy chain: EMBL accession No. J00461; light chain: EMBL accession No. V00807) to produce the full-length antibody gene, and then inserting it into an expression vector. Similarly, a recombinant rat-rabbit chimeric antibody AJ540 was produced by combining a known rabbit IgG (heavy chain: EMBL accession No. L29172, light chain: EMBL accession No. X00231) with the variable regions of the AJ540 antibody. The produced expression clone plasmids were introduced into HEK293 cells, large-scale culturing and purification with Protein A and gel filtration were performed, and recombinant mouse antibody AQ8 (rAQ8-mIgG2b) and recombinant rat-rabbit chimeric antibody AJ540 (rAJ540-rbtIgG) were produced.

Example 3 One-Stage Clotting Assay Carried Out Under Neutralization of the Anti-FIXa/FX Bispecific Antibody Using rAQ8-mIgG2b and rAJ540-rbtIgG To FVIII-deficient plasma (George King) containing 10 U/dL or 100 U/dL recombinant FVIII (Kogenate F S, Bayer Yakuhin, Ltd.), the anti-FIXa/FX bispecific antibody ACE910 was added at 0 μg/mL or 300 μg/mL. Furthermore, each of the prepared plasma samples was divided into the following two groups to prepare measurement sample solutions: a group subjected to ten-fold dilution using an imidazole buffer (Kyowa Medex); and a group subjected to ten-fold dilution using an imidazole buffer supplemented with 300 μg/mL each of rAQ8-mIgG2b and rAJ540-rbtIgG. Amounts of rAQ8-mIgG2b and rAJ540-rbtIgG required to sufficiently neutralize ACE910 were added. Details of the combinations are shown below.

TABLE 1

| Sample No. | Plasma Type | Dilution rate | Dilution buffer |
|---|---|---|---|
| #1 | FVIII deficient plasma containing 10 U/dL recombinant FVIII | 10-fold | Imidazole buffer |
| #2 | FVIII deficient plasma containing 10 U/dL recombinant FVIII | 10-fold | Imidazole buffer supplemented with rAQ8-mIgG2b and rAJ540-rbtIgG |
| #3 | FVIII deficient plasma containing 10 U/dL recombinant FVIII supplemented with 300 μg/mL anti-FIXa/FX bispecific antibody | 10-fold | Imidazole buffer |
| #4 | FVIII deficient plasma containing 10 U/dL recombinant FVIII supplemented with 300 μg/mL anti-FIXa/FX bispecific antibody | 10-fold | Imidazole buffer supplemented with rAQ8-mIgG2b and rAJ540-rbtIgG |
| #5 | FVIII deficient plasma containing 100 U/dL recombinant FVIII | 10-fold | Imidazole buffer |
| #6 | FVIII deficient plasma containing 100 U/dL recombinant FVIII | 10-fold | Imidazole buffer supplemented with rAQ8-mIgG2b and rAJ540-rbtIgG |
| #7 | FVIII deficient plasma containing 100 U/dL recombinant FVIII supplemented with 300 μg/mL anti-FIXa/FX bispecific antibody | 10-fold | Imidazole buffer |
| #8 | FVIII deficient plasma containing 100 U/dL recombinant FVIII supplemented with 300 μg/mL anti-FIXa/FX bispecific antibody | 10-fold | Imidazole buffer supplemented with rAQ8-mIgG2b and rAJ540-rbtIgG |

Furthermore, to produce a calibration curve for conversion of coagulation time to FVIII activity, solutions of standard plasma, Coagtrol N (Sysmex), were prepared by performing 10-fold, 20-fold, 40-fold, 80-fold, and 160-fold dilutions using an imidazole buffer (FVIII activities for the respective calibration curve solutions were specified as 93%, 46.5%, 23.3%, 11.6%, and 5.81%). Fifty microliters of a measurement sample solution or calibration curve solution, 50 μL of factor VIII-deficient human plasma (Sysmex), and 50 μL of Thrombocheck APTT-SLA (Sysmex) were mixed and incubated at 37° C. for five minutes. After incubation, 50 μL of 0.02 mol/L calcium chloride solution (Sysmex) was added to initiate coagulation, and the coagulation time was measured using automatic blood coagulation analyzer KC4 Delta (Stago).

Coagulation time of a measurement sample was converted to FVIII activity according to the coagulation time at each FVIII activity of the calibration curve solution.

Results

The results are shown in FIG. 1. When FVIII-deficient plasma containing 10 U/dL or 100 U/dL recombinant FVIII supplemented with an anti-FIXa/FX bispecific antibody was diluted with a buffer (#3, #7), the FVIII activities were shown to be above the range of the calibration curve, and could not be accurately measured. On the other hand, when FVIII-deficient plasma containing 10 U/dL or 100 U/dL recombinant FVIII supplemented with an anti-FIXa/FX bispecific antibody was diluted with a buffer containing two types of antibodies against the anti-FIXa/FX bispecific antibody (#4, #8), the FVIII activities were shown to be similar to those of the groups without addition of the anti-FIXa/FX bispecific antibody (#1, #5). Therefore, this shows that the antibodies against the anti-FIXa/FX bispecific antibody completely neutralized the activity of the bispecific antibody to enable accurate measurement of the FVIII activity in plasma even in the presence of the bispecific antibody. When FVIII-deficient plasma containing 10 U/dL or 100 U/dL recombinant FVIII was diluted with a buffer containing only the two types of antibodies against the anti-FIXa/FX bispecific antibody (#2, #6), the FVIII activities were shown to be similar to those of the groups without addition of the anti-FIXa/FX bispecific antibody (#1, #5); therefore, antibodies against the anti-FIXa/FX bispecific antibody were found to have neutralizing effects specific to the bispecific antibody.

Example 4 One-Stage Clotting Assay Carried Out Under Neutralization of the Anti-FIXa/FX Bispecific Antibody Using AQ1 and AJ541 or AQ1 and AJ522

To FVIII-deficient plasma (George King) containing 10 U/dL recombinant FVIII (Kogenate F S, Bayer Yakuhin, Ltd.), the anti-FIXa/FX bispecific antibody ACE910 was added at 0 μg/mL or 10 μg/mL. Furthermore, each of the prepared plasma was divided into three groups to prepare measurement sample solutions: a group subjected to ten-fold dilution using an imidazole buffer (Kyowa Medex); a group subjected to ten-fold dilution using an imidazole buffer supplemented with 100 μg/mL each of AQ1 and AJ541; and a group subjected to ten-fold dilution using an imidazole buffer supplemented with 100 μg/mL each of AQ1 and AJ522. Amounts of AQ1, AJ541 and AJ522 required to sufficiently neutralize ACE910 were added. Details of the combinations are shown below.

TABLE 2

| Sample No. | Plasma Type | Dilution rate | Dilution buffer |
|---|---|---|---|
| #1 | FVIII deficient plasma containing 10 U/dL recombinant FVIII | 10-fold | Imidazole buffer |
| #2 | | 10-fold | Imidazole buffer supplemented with AQ1 and AJ541 |
| #3 | | 10-fold | Imidazole buffer supplemented with AQ1 and AJ522 |
| #4 | FVIII-deficient plasma containing 10 U/dL recombinant FVIII supplemented with 10 μg/mL ACE910 | 10-fold | Imidazole buffer |
| #5 | | 10-fold | Imidazole buffer supplemented with AQ1 and AJ541 |
| #6 | | 10-fold | Imidazole buffer supplemented with AQ1 and AJ522 |

Furthermore, to produce a calibration curve for conversion of coagulation time to FVIII activity, solutions of standard plasma, Coagtrol N (Sysmex), were prepared by performing 10-fold, 20-fold, 40-fold, 80-fold, 160-fold, 320-fold and 640-fold dilutions using an imidazole buffer (FVIII activities for the respective calibration curve solutions were specified as 102%, 51.0%, 25.5%, 12.8%, 6.38%, 3.19% and 1.59%). Fifty microliters of a measurement sample solution or calibration curve solution, 50 μL of factor VIII-deficient human plasma (Sysmex), and 50 μL of Thrombocheck APTT-SLA (Sysmex) were mixed and incubated at 37° C. for five minutes. After incubation, 50 μL of 0.02 mol/L calcium chloride solution (Sysmex) was added to initiate coagulation, and the coagulation time was measured using automatic blood coagulation analyzer KC4 Delta (Stago).

Coagulation time of a measurement sample was converted to FVIII activity according to the coagulation time at each FVIII activity of the calibration curve solution.

Results

Figure 2:
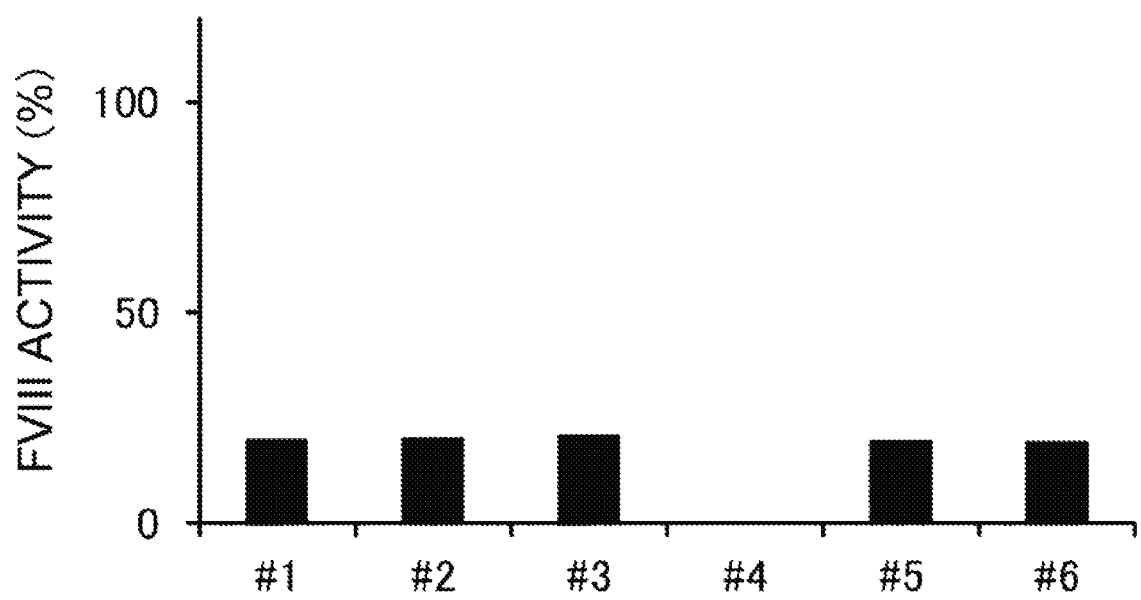
FIG. 2 shows the results of one-stage clotting assay performed under neutralization of the anti-FIXa/FX bispecific antibody with AQ1 and AJ541 or AQ1 and AJ522. When FVIII-deficient plasma containing 10 U/dL recombinant FVIII supplemented with an anti-FIXa/FX bispecific antibody, ACE910, was diluted with a buffer (#4), the FVIII activities were shown to be above the range of the calibration curve. On the other hand, when FVIII-deficient plasma containing 10 U/dL recombinant FVIII supplemented with the anti-FIXa/FX bispecific antibody ACE910 was diluted with a buffer containing two types of antibodies, AQ1 and AJ541, against the anti-FIXa/FX bispecific antibody (#5), or a buffer containing two types of antibodies, AQ1 and AJ522, against the anti-FIXa/FX bispecific antibody (#6), the FVIII activities were shown to be similar to those of the groups without addition of the anti-FIXa/FX bispecific antibody (#1). When FVIII-deficient plasma containing 10 U/dL recombinant FVIII was diluted with a buffer containing only the two types of antibodies, AQ1 and AJ541, against the anti-FIXa/FX bispecific antibody (#2), or a buffer containing only the two types of antibodies, AQ1 and AJ522 (#3), the FVIII activities were shown to be similar to those of the groups without addition of the anti-FIXa/FX bispecific antibody (#1).

The results are shown in FIG. 2. When FVIII-deficient plasma containing 10 U/dL recombinant FVIII supplemented with an anti-FIXa/FX bispecific antibody, ACE910, was diluted with a buffer (#4), the FVIII activity was shown to be above the range of the calibration curve, and could not be accurately measured. On the other hand, when FVIII-deficient plasma containing 10 U/dL recombinant FVIII supplemented with an anti-FIXa/FX bispecific antibody, ACE910, was diluted with a buffer containing two types of antibodies, AQ1 and AJ541, against the anti-FIXa/FX bispecific antibody (#5) or a buffer containing two types of antibodies, AQ1 and AJ522, against the anti-FIXa/FX bispecific antibody (#6), the FVIII activity was shown to be similar to that of the group without addition of the anti-FIXa/FX bispecific antibody (#1). Therefore, this shows that not only rAQ8-mIgG2b and rAJ540-rbtIgG, but other antibody combinations are also effective as antibodies against the anti-FIXa/FX bispecific antibody to completely neutralize the activity of the bispecific antibody ACE910.

Example 5 One-Stage Clotting Assay Carried Out Under Neutralization of the Anti-FIXa/FX Bispecific Antibody Using AQ512 and AJ114 or AQ512 and AJ521

To FVIII-deficient plasma (George King) containing 10 U/dL recombinant FVIII (Kogenate F S, Bayer Yakuhin, Ltd.), the anti-FIXa/FX bispecific antibody hBS23 was added at 0 μg/mL or 10 μg/mL. Furthermore, each of the prepared plasma was divided into three groups to prepare measurement sample solutions: a group subjected to ten-fold dilution using an imidazole buffer (Kyowa Medex); a group subjected to ten-fold dilution using an imidazole buffer supplemented with 100 μg/mL each of AQ512 and AJ114; and a group subjected to ten-fold dilution using an imidazole buffer supplemented with 100 μg/mL each of AQ512 and AJ521. Amounts of AQ512, AJ114, and AJ521 required to sufficiently neutralize hBS23 were added. Details of the combinations are shown below.

TABLE 3

| Sample No. | Plasma Type | Dilution rate | Dilution buffer |
|---|---|---|---|
| #1 | FVIII-deficient plasma containing 10 U/dL recombinant FVIII | 10-fold | Imidazole buffer |
| #2 | | 10-fold | Imidazole buffer supplemented with AQ512 and AJ114 |
| #3 | | 10-fold | Imidazole buffer supplemented with AQ512 and AJ521 |
| #4 | FVIII-deficient plasma containing 10 U/dL recombinant FVIII supplemented with 10 μg/mL hBS23 | 10-fold | Imidazole buffer |
| #5 | | 10-fold | Imidazole buffer supplemented with AQ512 and AJ114 |
| #6 | | 10-fold | Imidazole buffer supplemented with AQ512 and AJ521 |

Furthermore, to produce a calibration curve for conversion of coagulation time to FVIII activity, solutions of standard plasma, Coagtrol N (Sysmex), were prepared by performing 10-fold, 20-fold, 40-fold, 80-fold, 160-fold, 320-fold and 640-fold dilutions using an imidazole buffer (FVIII activities for the respective calibration curve solutions were specified as 102%, 51.0%, 25.5%, 12.8%, 6.38%, 3.19% and 1.59%). Fifty microliters of a measurement sample solution or calibration curve solution, 50 μL of factor VIII-deficient human plasma (Sysmex), and 50 μL of Thrombocheck APTT-SLA (Sysmex) were mixed and incubated at 37° C. for five minutes. After incubation, 50 μL of 0.02 mol/L calcium chloride solution (Sysmex) was added to initiate coagulation, and the coagulation time was measured using automatic blood coagulation analyzer KC4 Delta (Stago).

Coagulation time of a measurement sample was converted to FVIII activity according to the coagulation time at each FVIII activity of the calibration curve solution.

Results

Figure 3:
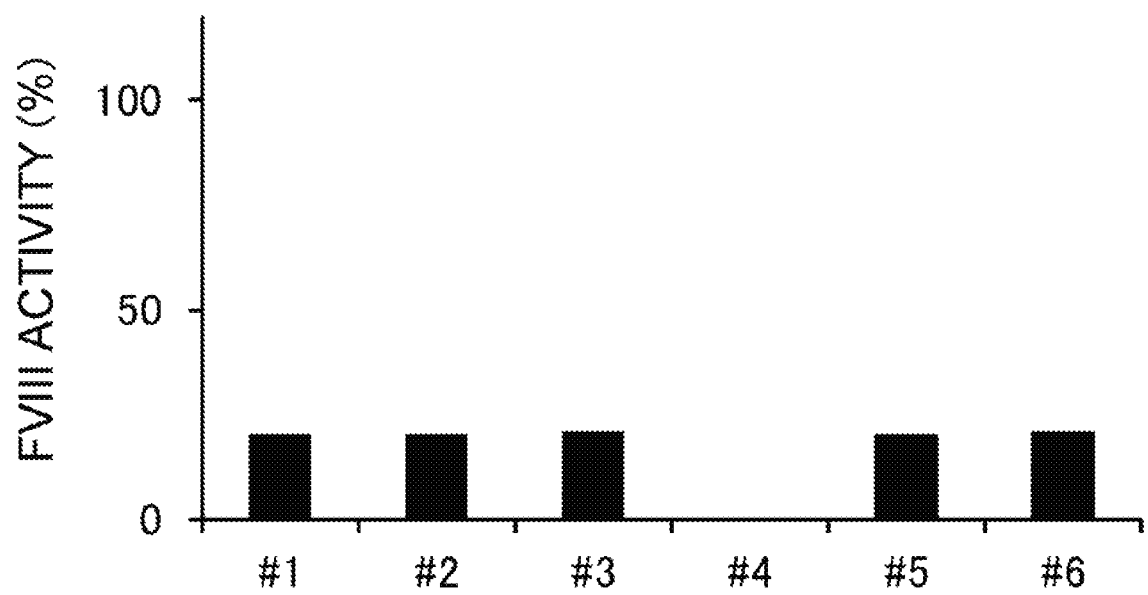
FIG. 3 shows the results of one-stage clotting assay performed under neutralization of the anti-FIXa/FX bispecific antibody with AQ512 and AJ114 or AQ512 and AJ521. When FVIII-deficient plasma containing 10 U/dL recombinant FVIII supplemented with an anti-FIXa/FX bispecific antibody, hBS23, was diluted with a buffer (#4), the FVIII activities were shown to be above the range of the calibration curve. On the other hand, when FVIII-deficient plasma containing 10 U/dL recombinant FVIII supplemented with the anti-FIXa/FX bispecific antibody hBS23 was diluted with a buffer containing two types of antibodies, AQ512 and AJ114, against the anti-FIXa/FX bispecific antibody (#5), or a buffer containing two types of antibodies, AQ512 and AJ521, against the anti-FIXa/FX bispecific antibody (#6), the FVIII activities were shown to be similar to those of the groups without addition of the anti-FIXa/FX bispecific antibody (#1). When FVIII-deficient plasma containing 10 U/dL recombinant FVIII was diluted with a buffer containing only the two types of antibodies, AQ512 and AJ114, against the anti-FIXa/FX bispecific antibody (#2), or a buffer containing only the two types of antibodies, AQ512 and AJ521 (#3), the FVIII activities were shown to be similar to those of the groups without addition of the anti-FIXa/FX bispecific antibody (#1).

The results are shown in FIG. 3. When FVIII-deficient plasma containing 10 U/dL recombinant FVIII supplemented with an anti-FIXa/FX bispecific antibody, hBS23, was diluted with a buffer (#4), the FVIII activity was shown to be above the range of the calibration curve, and could not be accurately measured. On the other hand, when FVIII-deficient plasma containing 10 U/dL recombinant FVIII supplemented with an anti-FIXa/FX bispecific antibody, hBS23, was diluted with a buffer containing two types of antibodies, AQ512 and AJ114, against the anti-FIXa/FX bispecific antibody (#5) or a buffer containing two types of antibodies, AQ512 and AJ521, against the anti-FIXa/FX bispecific antibody (#6), the FVIII activity was shown to be similar to that of the group without addition of the anti-FIXa/FX bispecific antibody (#1). These show that even with hBS23, a bispecific antibody different from ACE910, the FVIII activity in plasma can be accurately measured despite the presence of the bispecific antibody by completely neutralizing its activity, and therefore the present approach is effective for various bispecific antibodies that have FVIII-substituting activity.

Example 6 Bethesda Assay Carried Out Under Neutralization of the Anti-FIXa/FX Bispecific Antibody Using rAQ8-mIgG2b and rAJ540-rbtIgG To factor VIII-deficient human plasma (containing FVIII inhibitors) (George King Bio-Medical), anti-FIXa/FX bispecific antibody ACE910 was added at 0 μg/mL or 300 μg/mL. Furthermore, each of the prepared plasma samples was subjected to 25-fold dilution or 30-fold dilution using a 0.25% (w/v) bovine serum albumin (Sigma-Aldrich)-containing imidazole buffer (Kyowa Medex) (hereinafter referred to as BSA-imidazole). To Coagtrol N (Sysmex) which is standard plasma, rAQ8-mIgG2b and rAJ540-rbtIgG were either not added, or they were added at 300 μg/mL each.

Two types of the prepared plasma samples were mixed in equal amounts in the following combinations (a total of 8 types), and then subjected to incubation at 37° C. for two hours.

TABLE 4

| Sample No. | Plasma 1 Type | Dilution rate | Plasma 2 |
|---|---|---|---|
| #1 | Factor VIII-deficient human plasma (containing inhibitors) without addition of the anti-FIXa/FX bispecific antibody | 25-fold 30-fold | Coagtrol N without addition of rAQ8-mIgG2b and rAJ540-rbtIgG |
| #2 | | 25-fold 30-fold | Coagtrol N containing 300 μg/mL rAQ8-mIgG2b and 300 μg/mL rAJ540-rbtIgG |
| #3 | Factor VIII-deficient human plasma (containing inhibitors) containing 300 μg/mL anti-FIXa/FX bispecific antibody | 25-fold 30-fold | Coagtrol N without addition of rAQ8-mIgG2b and rAJ540-rbtIgG |
| #4 | | 25-fold 30-fold | Coagtrol N containing 300 μg/mL rAQ8-mIgG2b and 300 μg/mL rAJ540-rbtIgG |

After incubation, the mixed solutions were further diluted ten-fold with BSA-imidazole to prepare measurement sample solutions. Furthermore, to prepare a calibration curve for conversion of coagulation time to FVIII activity values, solutions were prepared by diluting Coagtrol N with BSA-imidazole at 20-fold, 40-fold, 80-fold, 160-fold, and 320-fold dilution (FVIII activities of the respective calibration curve solutions were specified as 100%, 50%, 25%, 12.5%, and 6.25%).

Fifty microliters of a measurement sample solution or calibration curve solution, 50 μL of factor VIII-deficient human plasma (Sysmex), and 50 μL of Thrombocheck APTT-SLA (Sysmex) were mixed and incubated at 37° C. for three minutes. After incubation, 50 μL of 0.02 mol/L calcium chloride solution (Sysmex) was added to initiate coagulation, and the coagulation time was measured using automatic blood coagulation analyzer KC4 Delta (Stago).

Coagulation time of a measurement sample was converted to FVIII activity according to the coagulation time at each FVIII activity of the calibration curve solution. Furthermore, when the residual FVIII activity was 50%, this was specified as 1 Bethesda, and after calculating the Bethesda values in the measurement sample, mean value calculated by multiplying the value by 25 or 30 was determined as the inhibitor titer in each of the original sample solutions.

Results

Figure 4:
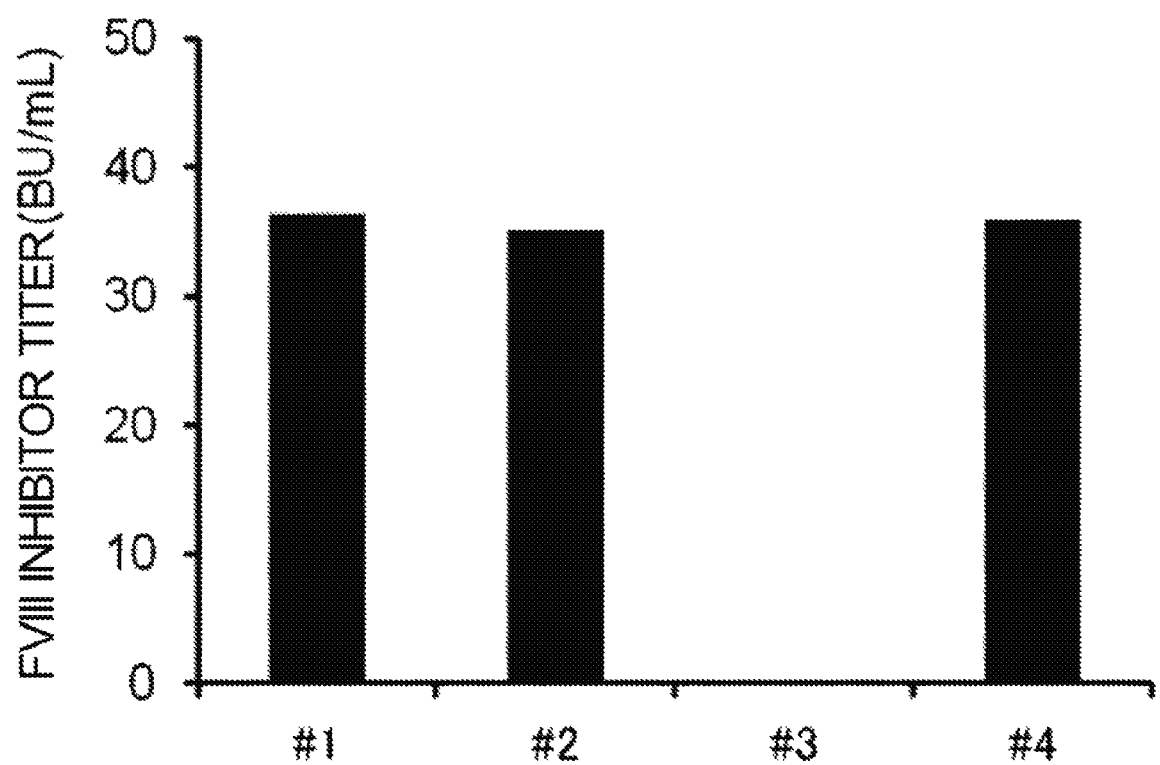
FIG. 4 shows the results of Bethesda assay performed under neutralization of the anti-FIXa/FX bispecific antibody using rAQ8-mIgG2b and rAJ540-rbtIgG. FVIII inhibitor plasma containing only the anti-FIXa/FX bispecific antibody ACE910 (#3) showed an activity equivalent to 100% or more of FVIII of the calibration curve. On the other hand, FVIII inhibitor plasma containing the anti-FIXa/FX bispecific antibody and the two types of antibodies against the anti-FIXa/FX bispecific antibody (#4) showed an FVIII inhibitor titer similar to that of the inhibitor plasma without additives (#1). FVIII inhibitor plasma containing only the two types of antibodies against the anti-FIXa/FX bispecific antibody (#2) showed results similar to that of #1.

The results are shown in FIG. 4. The FVIII inhibitor plasma containing only the anti-FIXa/FX bispecific antibody (#3) showed an activity that was 100% or more of FVIII of the calibration curve; therefore, the FVIII inhibitor titer could not be determined.

On the other hand, FVIII inhibitor plasma containing the anti-FIXa/FX bispecific antibody and the two types of antibodies against the anti-FIXa/FX bispecific antibody (#4) showed an FVIII inhibitor titer similar to that of the inhibitor plasma without additives (#1). Therefore, this shows that the antibodies against the anti-FIXa/FX bispecific antibody completely neutralized the activity of the bispecific antibody to enable accurate measurement of the FVIII inhibitor titer in plasma even in the presence of the bispecific antibody. FVIII inhibitor plasma containing only the two types of antibodies against the anti-FIXa/FX bispecific antibody (#2) showed similar results to that of #1; therefore, antibodies against the anti-FIXa/FX bispecific antibody were found to have neutralizing effects specific to the bispecific antibody.

INDUSTRIAL APPLICABILITY

The present invention provides methods for measuring the reactivity of FVIII in the presence of a bispecific antibody having an activity of functionally substituting for FVIII, for example, methods for measuring FVIII activity or FVIII inhibitor titer. Use of the methods of the present invention enables accurate measurement of the reactivity of FVIII in patients during treatment of hemorrhagic diseases, such as hemophilia, by using the bispecific antibody.

The invention claimed is:

1. A method for determining a level of coagulation factor VIII (FVIII) activity or FVIII inhibitor titer in a sample from a patient who had been treated with a bispecific antibody functionally substituting for FVIII, the method comprising:
   (i) providing an in vitro sample derived from blood of the patient and containing the bispecific antibody, wherein the bispecific antibody is any one of the bispecific antibodies recited below, in which a first polypeptide is associated with a third polypeptide and a second polypeptide is associated with a fourth polypeptide:
   a bispecific antibody in which the first polypeptide is an H chain consisting of the amino acid sequence of SEQ ID NO: 9, the second polypeptide is an H chain consisting of the amino acid sequence of SEQ ID NO: 11, and the third and fourth polypeptides are identical L chains, each consisting of the amino acid sequence of SEQ ID NO: 10; or a bispecific antibody in which the first polypeptide is an H chain consisting of the amino acid sequence of SEQ ID NO: 36, the second polypeptide is an H chain consisting of the amino acid sequence of SEQ ID NO: 37, and the third and fourth polypeptides are identical L chains, each consisting of the amino acid sequence of SEQ ID NO: 38;

(ii) contacting the sample with one or more antibodies that neutralize the bispecific antibody so that it does not functionally substitute for FVIII; and (iii) assaying the sample to determine a level of FVIII activity or a level of FVIII inhibitor titer in the sample, wherein at least one of the one or more antibodies that neutralize the bispecific antibody is selected from the group consisting of:

(A) an antibody having a heavy chain variable region comprising a CDR1 comprising the amino acid sequence of SEQ ID NO: 12, a CDR2 comprising the amino acid sequence of SEQ ID NO: 13, and a CDR3 comprising the amino acid sequence of SEQ ID NO: 14; and a light chain variable region comprising a CDR1 comprising the amino acid sequence of SEQ ID NO: 18, a CDR2 comprising the amino acid sequence of SEQ ID NO: 19, and a CDR3 comprising the amino acid sequence of SEQ ID NO: 20, (B) an antibody having a heavy chain variable region comprising the amino acid sequence of SEQ ID NO: 1 and a light chain variable region comprising the amino acid sequence of SEQ ID NO: 2, (C) an antibody having a heavy chain variable region comprising a CDR1 comprising the amino acid sequence of SEQ ID NO: 24, a CDR2 comprising the amino acid sequence of SEQ ID NO: 25, and a CDR3 comprising the amino acid sequence of SEQ ID NO: 26; and a light chain variable region comprising a CDR1 comprising the amino acid sequence of SEQ ID NO: 30, a CDR2 comprising the amino acid sequence of SEQ ID NO: 31, and a CDR3 comprising the amino acid sequence of SEQ ID NO: 32, and (D) an antibody having a heavy chain variable region comprising the amino acid sequence of SEQ ID NO: 3 and a light chain variable region comprising the amino acid sequence of SEQ ID NO: 4.

2. The method of claim 1, wherein step (ii) comprises contacting the sample with a combination of two antibodies that neutralize the bispecific antibody, the two antibodies being the antibodies of (A) and (C).

3. The method of claim 2, wherein, following the contacting step, the sample is assayed for FVIII activity.

4. The method of claim 3, wherein the FVIII activity is assayed with a one-stage clotting assay or a thrombin generation assay.

5. The method of claim 2, wherein, following the contacting step, the sample is assayed for FVIII inhibitor titer.

6. The method of claim 5, wherein the FVIII inhibitor titer is assayed with a Bethesda assay, an ELISA, or a Nijmegen Bethesda assay.

7. The method of claim 2, wherein the patient is a human patient who has a disease involving hemorrhagic symptoms, and to whom the bispecific antibody has been administered as a treatment for the disease, prior to obtaining the blood from the patient.

8. The method of claim 7, wherein, after the contacting step, the sample is assayed to determine FVIII activity.

9. The method of claim 8, wherein the FVIII activity determined in the sample is compared to FVIII activity in a control sample derived from blood obtained from a human subject who does not have the disease, and wherein the comparison provides an indication of the disease's severity in the patient.

10. The method of claim 7, wherein, after the contacting step, the sample is assayed to determine FVIII inhibitor titer.

11. The method of claim 10, wherein the patient is a hemophilia A patient whose plasma comprises an FVIII inhibitor.

12. The method of claim 7, wherein a formulation comprising FVIII was administered to the patient, prior to obtaining the blood from the patient.

13. The method of claim 1, wherein step (ii) comprises contacting the sample with a combination of two antibodies that neutralize the bispecific antibody, the two antibodies being the antibodies of (B) and (D).

14. The method of claim 13, wherein, following the contacting step, the sample is assayed for FVIII activity.

15. The method of claim 14, wherein the FVIII activity is assayed with a one-stage clotting assay or a thrombin generation assay.

16. The method of claim 13, wherein, following the contacting step, the sample is assayed for FVIII inhibitor titer.

17. The method of claim 16, wherein the FVIII inhibitor titer is assayed with a Bethesda assay, an ELISA, or a Nijmegen Bethesda assay.

18. The method of claim 1, wherein one of the one or more antibodies that neutralize the bispecific antibody binds to a Fab comprising the variable regions of SEQ ID NOs: 9 and 10.

19. The method of claim 1, wherein one of the one or more antibodies that neutralize the bispecific antibody binds to a Fab comprising the variable regions of SEQ ID NOs: 11 and 10.

20. The method of claim 1, wherein one of the one or more antibodies is the antibody of (A).

21. The method of claim 1, wherein one of the one or more antibodies is the antibody of (B).

22. The method of claim 1, wherein one of the one or more antibodies is the antibody of (C).

23. The method of claim 1, wherein one of the one or more antibodies is the antibody of (D).

24. The method of claim 1, wherein, following the contacting step, the sample is assayed for FVIII activity.

25. The method of claim 24, wherein the FVIII activity is assayed with a one-stage clotting assay or a thrombin generation assay.

26. The method of claim 1, wherein, following the contacting step, the sample is assayed for FVIII inhibitor titer.

27. The method of claim 26, wherein the FVIII inhibitor titer is assayed with a Bethesda assay, an ELISA, or a Nijmegen Bethesda assay.

28. The method of claim 1, wherein the patient is a human patient who has a disease involving hemorrhagic symptoms, and to whom the bispecific antibody has been administered as a treatment for the disease, prior to obtaining the blood from the patient.

29. The method of claim 28, wherein, after the contacting step, the sample is assayed to determine FVIII activity.

30. The method of claim 29, wherein the FVIII activity determined in the sample is compared to FVIII activity in a control sample derived from blood obtained from a human subject who does not have the disease, and wherein the comparison provides an indication of the disease's severity in the patient.

31. The method of claim 28, wherein, after the contacting step, the sample is assayed to determine FVIII inhibitor titer.

32. The method of claim 28, wherein a formulation comprising FVIII was administered to the patient, prior to obtaining the blood from the patient.

33. The method of claim 28, wherein the patient is selected from the group consisting of a hemophilia A patient, an acquired hemophilia A patient, and a von Willebrand disease patient.

34. The method of claim 31, wherein the patient is a hemophilia A patient whose plasma comprises an FVIII inhibitor.

* * * * *